(12) United States Patent
Tracey et al.

(10) Patent No.: US 6,391,899 B1
(45) Date of Patent: *May 21, 2002

(54) COMPOUNDS AND COMPOSITIONS FOR TREATING TISSUE ISCHEMIA

(75) Inventors: Kevin J. Tracey, Old Greenwich, CT (US); Yousef Al-Abed, New York; Svetlana Ivanova, Astoria, both of NY (US); Richard J. Bucala, Cos Cob, CT (US)

(73) Assignee: North Shore—Long Island Jewish Research Institute, Manhasset, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/118,388

(22) Filed: Jul. 17, 1998

(51) Int. Cl.$^7$ .............................................. A01N 43/40
(52) U.S. Cl. ....................................... 514/358; 546/342
(58) Field of Search ........................... 546/342; 514/358

(56) References Cited

U.S. PATENT DOCUMENTS 5,223,510 A * 6/1993 Gubin ........................ 514/299

OTHER PUBLICATIONS

Tamura J.C.S. Perkin I, 2091–5 1973.*
Litvinenko Zh.Org.Khim 3(5) 936–42, May 1967.*

* cited by examiner

*Primary Examiner*—Robert Gerstl
(74) *Attorney, Agent, or Firm*—Amster, Rothstein & Ebenstein

(57) ABSTRACT

There is disclosed a genus of compounds and pharmaceutical compositions that are protective for mitigating damage associated with tissue ischemia, particularly stroke (CNS ischemia), and ischemia of the myocardium. The present invention further provides a method for treating tissue damage caused by ischemia. Lastly, the present invention provides a method for treating tissue damage caused by providing a compound that inhibits the cytotoxic activity of 3-aminopropanal.

25 Claims, 8 Drawing Sheets

COMPOUNDS AND COMPOSITIONS FOR TREATING TISSUE ISCHEMIA

TECHNICAL FIELD OF THE INVENTION

The present invention provides a genus of compounds and pharmaceutical compositions that are protective for mitigating damage associated with tissue ischemia, particularly stroke (CNS ischemia), and ischemia of the myocardium. The present invention further provides a method for treating or preventing tissue damage precipitated by injury, disease or insult, particularly the tissue damage caused by ischemia. Lastly, the present invention provides a method for treating or preventing tissue damage by providing compounds that and compositions that inhibit or neutralize the cytotoxic activity of 3-aminopropanal.

BACKGROUND OF THE INVENTION

Cerebral ischemia, a leading cause of disability and mortality world-wide, is mediated by a cascade of molecular cytotoxins that kill potentially viable cells in the brain. The polyamines, spermine, spermidine, and putrescine, which are among the most abundant molecules in mammalian brain, have been implicated in the pathogenesis of ischemic brain damage (Zhang et al., *Proc. Natl. Acad. Sci. USA* 91:10883–10887, 1994; Harman and Shaw, *Br. J. Pharmac.* 73:165–174, 1981; Bergeron et al., *J. Med. Chem.* 39:5257–5266, 1996; Glantz et al., *J. Basic. Clin. Physiol. Pharmacol.* 7:1–10, 1996; Dempsey et al., *Neurosurg.* 17:635–640, 1985; and Schmitz et al., *Neurosurg.* 33:882–888, 1993). Polyamine biosynthesis is increased following the onset of cerebral ischemia, due to an ischemia-mediated induction of ornithine decarboxylase, a key synthetic enzyme in the polyamine biosynthetic pathway. Spermine was linked to development of glutamate-mediated cytotoxicity, because it can bind to the NR1 subunit of the NMDA receptor and potentiate glutamate-mediated cell damage (Traynelis et al., *Science* 268:873–876, 1995; Traynelis and Cull-Candy. *J. Physiol. (Lond.)* 433:727–763, 1991; and Sullivan et al., *Neuron* 13:929–936, 1994). Administration of experimental therapeutics which inhibit ornithine decarboxylase limit the development of ischemic brain damage in experimental animal models of stroke [ref]. Thus, the accumulation of polyamines in the ischemic brain occupies an important role in the pathogenesis of stroke (Kindy et al., *J. Cereb. Blood Flow Metab.* 14:1040–1045, 1994).

Brain spermine and spermidine levels are actually decreased by cerebral ischemia (Paschen, *J. Neurochem.* 49:35–37, 1987; and Paschen, *Cerebrovasc. Brain Metab. Rev.* 4:59–88, 1992). This observed decline of tissue spermine and spermidine levels is accompanied by an increase in brain levels of putrescine (Paschen, *Mol. Chem. Neuropathol.* 16:241–271, 1992; Paschen, *Cerebrovasc. Brain Metab. Rev.* 4:59–88, 1992; Morgan, Bachrach and Heimer, eds. CRC Publications, 203–229, 1989; and Paschen et al., *Acta Neuropathol.* 76:388–394, 1988). Further, intracerebral putrescine levels correlated significantly with the volume of brain cell death. Putrescine does not interact with the NMDA receptor, and does not potentiate its cytotoxic activity. A possible explanation for these results may reside in the catabolism of polyamines via the "interconversion pathway" which is dependent upon the activity of tissue polyamine oxidase (Seiler and Bolkenius, *Neurochem. Res.* 10:529–544, 1985; Seiler et al., *Med. Biol.* 59:334–346, 1981; Bolkenius and Seiler, *Int. J. Dev. Neurosci.* 4:217–224, 1986; and Bolkenius et al., *Biochim. Biophys. Acta* 838:69–76, 1985). This ubiquitous enzyme, which is present in high levels in brain and other mammalian tissues, cleaves spermine and spermidine via oxidative deamination to generate the end products putrescine and 3-aminopropanal (Seiler and Bolkenius, *Neurochem. Res.* 10:529–544, 1985; Seiler, In Yu et al., eds. Elsevier Science, 333–344, 1995; Morgan, *Essays in Biochemistry* 23:82–115, 1987; and Houen et al., *Acta Chem. Scand.* 48:52–60, 1994). 3-Aminopropanal is known for its cytotoxicity to primary endothelial cells, fibroblasts, and a variety of transformed mammalian cell lines (Bouzyk and Rosiek, *Cancer Lett.* 39:93–99, 1988; Brunton et al., *Toxic. in Vitro* 8:337–341, 1994; Gaugas and Dewey, *Br. J. Cancer* 39:548–557, 1978; Morgan et al., *J. Biochem.* 236:97–101, 1986; and Ferrante et al., *J. Immunol.* 133:2157–2162, 1984). 3-Aminopropanal has also been implicated as a mediator of programmed cell death in murine embryonic limb buds, and may contribute to the development of necrosis in some tumors (Parchment and Pierce, *Cancer Res* 49:6680–6686, 1989; and Kurihara et al., *Neurosurg.* 32:372–375, 1993). Inhibition of polyamine oxidase with aminoguanidine blocked generation of 3-aminopropanal in cell cultures following the addition of spermine, and prevented subsequent cytotoxicity (Ferrante et al., *J. Immunol.* 133:2157–2162, 1984; Morgan, *Essays in Biochemistry* 23:82–115, 1987; and Parchment and Pierce, *Cancer Res.* 49:6680–6686, 1989). On a molar basis, the $LD_{50}$ concentration of 3-aminopropanal to cells is similar to the cytotoxicity of glutamate. In contrast, putrescine is not cytotoxic to cells, even in the millimolar range, but its rate of production through polyamine oxidation correlates directly with the formation of a directly cytotoxic aldehyde, 3-aminopropanal.

In addition, in the data first being reported herein in glial cells, 3-aminopropanal mediates apoptosis by activation of an interleukin-1 beta converting enzyme (ICE)-dependent signaling pathway, whereas in neurons it causes necrotic cell death.

Cerebral ischemia (stroke) is a debilitating condition resulting from a sudden cessation of blood flow to an area of the brain, resulting in a loss of brain tissue. There are no available therapies to reverse the neurological deficits caused by neuronal death in the infarct zone. Stroke is a major public health problem in the United States wherein about 550,000 strokes occur each year. Cerebral ischemia afflicts individuals of all age groups, but the incidence doubles with each decade over 45 and reaches 1–2% per year in the population of individuals over 75 years of age. If a patient survives, major disability can result with loss of ability to communicate, ambulate, see, coordinate and/or reason. Standard therapy is often ineffective at preventing brain infarction and is meant to support cardiovascular and respiratory function, control intracranial pressure, and prevent recurrent stroke. There is also a class of protease enzymes that are designed to dissolve blood clots, only for those strokes caused by blood clots potentially useful in brain ischemia but (as opposed to bleeding) and these agents only function to restore some blood flow in limited situations.

During the evolution of cerebral infarction (stroke), a core of densely ischemic tissue becomes rapidly and irreversibly damaged. Cellular damage in the surrounding area, termed the "ischemic penumbra," progresses more slowly.

Following an ischemic insult, the process of tissue destruction may not be completed for hours or even days (Kirino et al., *Acta Neuropathol.* 64:139–147, 1984; and Petito et al. *Neurology* 37:1281–1286, 1987). There is a temporary window of opportunity for an intervention to prevent ischemic tissue from progressing to infarction. In humans, this window is thought to extend from about 2–4 hours following the onset of ischemia, after which time the efficacy decreases rapidly (Ginsberg and Pulsinelli, *Ann. Neurol.* 36:553–554, 1994). During the therapeutic window, the target for therapeutic neuroprotection is the ischemic penumbra, a volume of brain tissue around the ischaemic core, which receives reduced blood flow and contains compromised, but potentially viable tissue. Studies have identified important cytotoxic mediators that cause cell death in the early hours after the onset of ischemia.

A number of molecular substrates of normal brain, as well as extrinsic factors delivered by the circulation, contribute to the development of cell cytotoxicity during ischemia. These include, but are not limited to, glutamate, aspartate, nitric oxide, calcium, free radicals, zinc, cytokines, arachidonic acid metabolites, and advanced glycation end products (AGEs). Advanced glycation endproducts are a group of protein modifying adducts that were implicated in the pathogenesis of diabetic complications. AGEs were found to be cerebrotoxic in the ischemic penumbra (Zimmerman et al., *Proc. Natl. Acad. Sci. USA* 92:3744–3748, 1995). In addition, aminoguanidine, a small molecule inhibitor of AGE cross-linking reactions, effectively abrogated the cerebrotoxicity of AGEs during focal cerebral ischemia (Zimmerman et al., *Proc. Natl. Acad. Sci. USA* 92:3744–3748, 1995). Aminoguanidine was also found to be cerebroprotective during focal ischemia in normal, non-diabetic animals, independent of exogenous AGEs (Zimmerman et al., *Surg. Forum.* 45:600–603, 1994). Aminoguanidine further provided cerebroprotection in a model of focal stroke when administered within 2 hours after the onset of focal cerebral ischemia (Cockroft et al., *Stroke* 27:1393–1398, 1996). It was considered that the mechanism of action was inhibition of polyamine oxidase (PAO), an enzyme that produces toxic, reactive aldehyde metabolites by oxidation of biogenic amines.

The cascade of cytotoxicity that is initiated by reduced blood flow is followed by a drop in ATP levels and a reduction of oxidative phosphorylation. As a result, membrane potentials fall, leading to release of $K^+$ and an excessive amount of glutamate and other excitatory amino acids (EAAs) in a process called excitotoxicity. This will, in turn, over-activate N-methyl-D-aspartate (NMDA), amino-3-hydroxy-5-methyl-4-isoxasole-4-propionate (AMPA), kainate (KA), and 1S,3R-trans-1-amino-cyclopentyl-1,3dicarboxylate (trans-ACPD) receptors (Faroquil and Horrocks, *Brain Res.* 16:171–191, 1991).

Elevated glutamate leads to excessive $Ca^{2+}$ influx, primarily by excitatory amino acid receptor channel activation, as well as swelling and osmotic lysis as a result of depolorization mediated influx of $Na^+$, $Cl^-$ and water (Faroquil and Horrocks, *Brain Res.* 16:171–191, 1991). This elevation of intracellular $Ca^{2+}$ activates phospholipases, lipases, proteases and protein kinases, leading to eventual breakdown of phospholipid membranes, cytoskeletal alterations, arachidonic acid release, and potentiation of the free radical cascade (Manfred et al., *Biochem. Pharm.* 50:1–16, 1995). Other modulators of NMDA receptors include $Zn^{2+}$, histamine, certain neuroactive steroids, arachidonic acid, polyamines and protons or pH (Collinridge and Lester, *Pharmacol. Rev.* 74:143–210, 1989; and McBain and Mayer, *Physiol. Rev.* 74:723–760, 1994). Moreover, an NMDA receptor antagonist, MK-801, can exert a neuroprotective effect in animal models of cerebral ischemia (Olney et al., *J. Neurosci.* 9:1701–1704, 1989).

Ischemia also leads to formation of reactive oxygen species (ROS), activation of lipid peroxidation, and a reduction in the endogenous antioxidants ascorbate, glutathione, ubiquinone and α-tocopherol in brain tissue. The mitochondrial respiratory chain and reaction sequences catalyzed by cyclooxygenase and lipoxygenase are important production sites for superoxide anion ($O_2^-$), hydrogen peroxide ($H_2O_2$) and hydroxy radical ($OH^-$). Activated oxygen species are also formed during autooxidation of catecholamines and in the xanthine reaction.

Nitric oxide (NO) is another mediator of tissue injury in cerebral ischemia. NO concentrations increase acutely in the brain after middle cerebral artery (MCA) occlusion, from approximately 10 nM to 2.2 μM by a porphyrinc microsensor assay (Beckman et al., *Proc. Natl. Acad. Sci. USA* 87:1620, 1990).

In addition to these other suspected mediators of ischemic tissue damage, 3-aminopropanol is an enzymatic by-product of the oxidative cleavage of the polyamines spermine and spermidine by PAO in mammalian cells (Holtta, *Biochemistry* 16:91–100, 1997). The cytotoxicity resulting from co-incubation of PAO activity with spermine and spermidine has been abolished by aminoguanidine (Gabl et al., *Chemicobiological Interactins* 22:91–98, 1978; and Henle et al., *Cancer Res.* 46:175–182, 1986). 3-Aminopropanal has also been implicated in causing programmed cell death in murine embryonic limits buds (Parchment et al., *Cancer Res. Arch.* 49:6680–6686, 1989) and in necrosis of solid tumors.

These data provides a need in the art to find inhibitors of PAO activity that are likely to have therapeutic utility in treating tissue ischemia, particularly mitigating damage to the ischemic penumbra experienced in stroke, but also in non-neuronal tissue such as muscle tissue (e.g., smooth muscle and cardiac muscle).

SUMMARY OF THE INVENTION

The present invention provides a stroke-damage mitigating compound having a formula I:

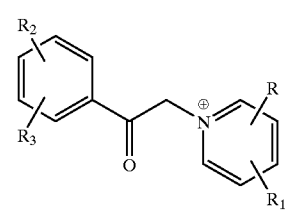

wherein R and $R_1$ are independently hydrogen, sulfamide, carboxyamide, cyano, straight or branched $C_{1-6}$ alkyl, straight or branched $C_{2-6}$ alkenyl, straight or branched $C_{1-6}$ alkoxy, a straight chain $C_{1-6}$ alkyl or a straight chain $C_{2-6}$ alkenyl having an ether link or an ester link, toluenyl, COOH, nitrate, or halide (Br, Cl, I, F), wherein both R and $R_1$ cannot be hydrogen, wherein $R_2$ and $R_3$ are independently hydrogen, sulfamide, carboxyamide, cyano, straight or branched $C_{1-6}$ alkyl, straight or branched $C_{2-6}$ alkenyl, straight or branched $C_{1-6}$ alkoxy, a straight chain $C_{1-6}$ alkyl or a straight chain $C_{2-6}$ alkenyl having an ether link or an ester link, toluenyl, COOH, nitrate, or halide (Br, Cl, I, F).

Preferably, R and $R_1$ are meta to each other and to the heteroatom. Preferably, R is COOH. Preferably, $R_1$ is COOH. Preferably, $R_2$ and $R_3$ are both hydrogen. Most preferably, R and $R_1$ are each COOH, and $R_2$ and $R_3$ are both hydrogen.

Preferred compounds of formula I include, for example, 1-phenacyl-2,3-dicarboxypyridinium bromide; 1-phenacyl- 2,4-dicarboxypyridinium bromide; 1-phenacyl-2,5-dicarboxypyridinium bromide; 1-phenacyl-2,6-dicarboxypyridinium bromide; 1-phenacyl-2,3-dicarboxyimidepyridinium bromide; 1-phenacyl-2,4-dicarboxyimidepyridinium bromide; 1-phenacyl-2,5-dicarboxyimidepyridinium bromide; and 1-phenacyl-2,6-dicarboxyimidepyridinium bromide; 1-phenacyl-2,3-dicarboxyimidepyrdinium bromide; 1-phenacyl-2,4-dicarboxyimidepyrdinium bromide; 1-phenacyl-2,5-dicarboxyimidepyrdinium bromide; and 1-phenacyl-2,6-dicarboxyimidepyrdinium bromide.

The present invention provides a pharmaceutical composition comprising a compound from formula I in a pharmaceutically acceptable carrier, wherein formula I comprises:

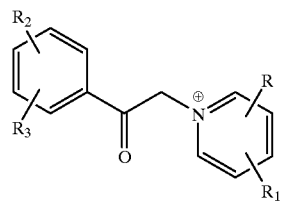

I wherein R and $R_1$ are independently hydrogen, sulfamide, carboxyamide, cyano, straight or branched $C_{1-6}$ alkyl, straight or branched $C_{2-6}$ alkenyl, straight or branched $C_{1-6}$ alkoxy, a straight chain $C_{1-6}$ alkyl or a straight chain $C_{2-6}$ alkenyl having an ether link or an ester link, toluenyl, COOH, nitrate, or halide (Br, Cl, I, F), wherein both R and $R_1$ cannot be hydrogen, wherein $R_2$ and $R_3$ are independently hydrogen, sulfamide, carboxyamide, cyano, straight or branched $C_{1-6}$ alkyl, straight or branched $C_{2-6}$ alkenyl, straight or branched $C_{1-6}$ alkoxy, a straight chain $C_{1-6}$ alkyl or a straight chain $C_{2-6}$ alkenyl having an ether link or an ester link, toluenyl, COOH, nitrate, or halide (Br, Cl, I, F).

Preferably, R and $R_1$ are meta to each other and to the heteroatom. Preferably, R is COOH. Preferably, $R_1$ is COOH. Preferably, $R_2$ and $R_3$ are both hydrogen. Most preferably, R and $R_1$ are each COOH, $R_2$ and $R_3$ are both hydrogen.

The present invention further provides a method for treating tissue ischemia to mitigate ischemic damage, comprising administering an effective amount of a compound of formula I, wherein formula I comprises:

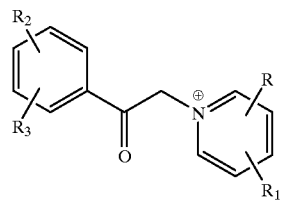

I wherein R and $R_1$ are independently hydrogen, sulfamide, carboxyamide, cyano, straight or branched $C_{1-6}$ alkyl, straight or branched $C_{2-6}$ alkenyl, straight or branched $C_{1-6}$ alkoxy, a straight chain $C_{1-6}$ alkyl or a straight chain $C_{2-6}$ alkenyl having an ether link or an ester link, toluenyl, COOH, nitrate, or halide (Br, Cl, I, F), wherein both R and $R_1$ cannot be hydrogen, wherein $R_2$ and $R_3$ are independently hydrogen, sulfamide, carboxyamide, cyano, straight or branched $C_{1-6}$ alkyl, straight or branched $C_{2-6}$ alkenyl, straight or branched $C_{1-6}$ alkoxy, a straight chain $C_{1-6}$ alkyl or a straight chain $C_{2-6}$ alkenyl having an ether link or an ester link, toluenyl, COOH, nitrate, or halide (Br, Cl, I, F).

Preferably, R and $R_1$ are meta to each other and to the heteroatom. Preferably, R is COOH. Preferably, $R_1$ is COOH. Preferably, $R_2$ and $R_3$ are both hydrogen. Most preferably, R and $R_1$ are each COOH, and $R_2$ and $R_3$ are both hydrogen.

The invention further provides a method for treating tissue ischemia to mitigate ischemic damage, comprising administering an effective amount of a compound of formula II, wherein formula II comprises:

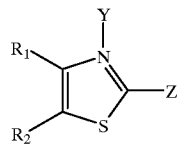

II wherein $R_1$ and $R_2$ are independently selected from the group consisting of hydrogen, hydroxy $C_{1-6}$ alkyl, $C_{1-6}$ alkoxy $C_{1-6}$ alkyl, and $R_1$ and $R_2$ together with their ring carbons may be an aromatic fused ring; wherein Z is hydrogen or an amino group; wherein Y is hydrogen or a group of the formula —$CH_2COR$; wherein R is $C_{1-6}$ alkyl, $C_{1-6}$ alkoxy, hydroxy, amino, aryl, or —$CH_2R_3$ wherein $R_3$ is H, $C_{1-6}$ alkyl, $C_{2-6}$ alkenyl, or $C_{4-6}$ aryl. Preferably, the compound of formula II is a halide (Cl, Br, F or I), tosylate, methanesulfonate or mesitylene sulfonate salt.

The present invention further provides a method for inhibiting tissue damage, comprising administering an effective amount of a compound that inhibits or neutralizes the cytotoxic activity of 3-aminopropanal. Preferably, the diseases resulting from tissue ischemia are myocardial infarction or stroke.

DETAILED DESCRIPTION OF THE INVENTION

The present invention arose out of a series of experiments wherein cerebral damage subsequent to induced focal ischemia was found to be mediated by the induction of brain polyamine oxidase activity. Moreover, the cytotoxic end product 3-aminopropanal accumulated in the ischemic brain at levels that are lethal to neurons and glial cells. These data further demonstrated that inhibition of polyamine oxidase activity with structurally distinct pharmaceutical compounds prevented the formation of 3-aminopropanal, and provided significant protection against the development of cerebral damage following permanent cerebral artery occlusion in rats. Finally, data is presented that certain compounds with the potential to react with 3-aminopropanal are efficacious in limiting the extent of tissue damage following ischemia 3-Aminopropanal.

Figure 2:
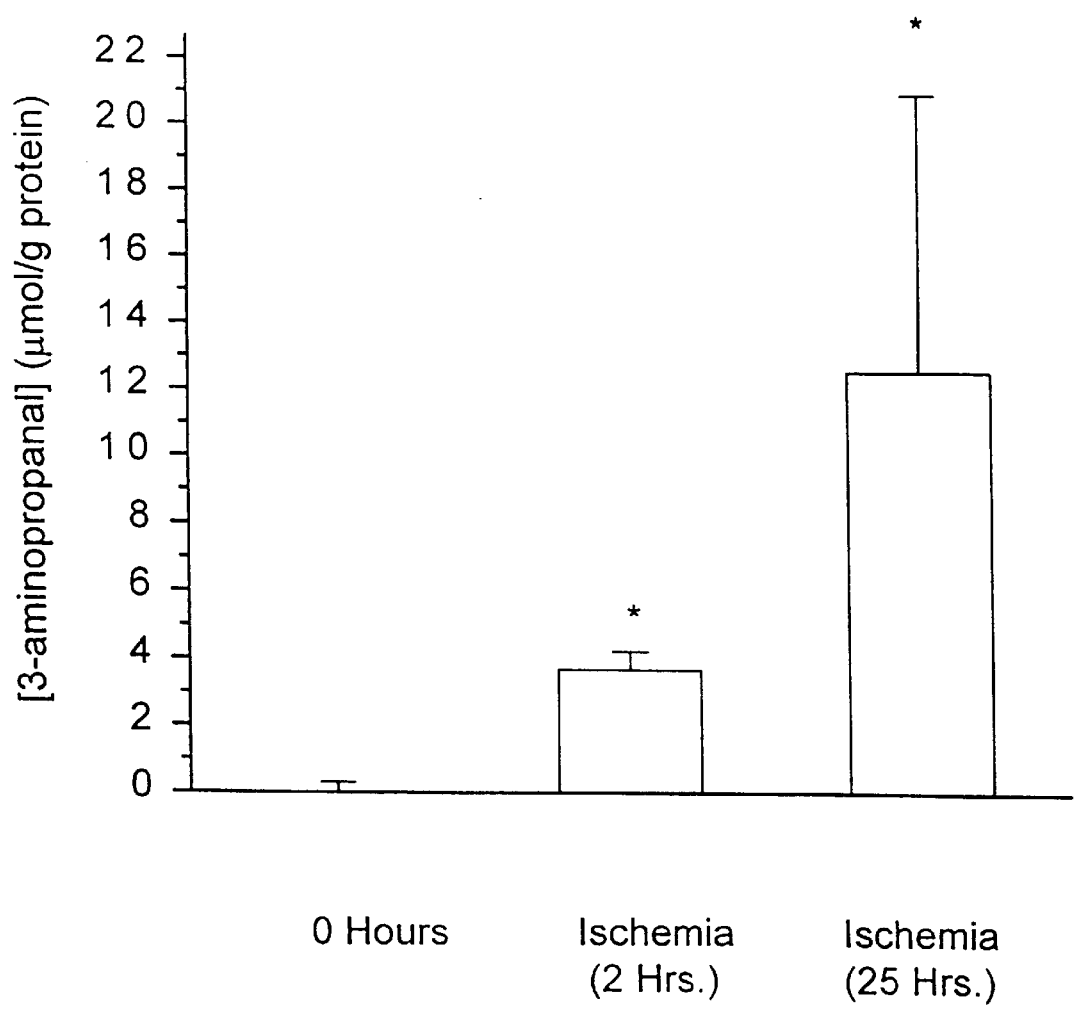
FIG. 2 shows that brain 3-aminopropanal levels increase during cerebral ischemia. Brain 3-aminopropanal levels were measured by derivatization and HPLC assay (as described infra) in rats subjected to permanent focal cerebral ischemia 3-Aminopropanal was not detected in sham-operated controls. It should be noted that 3-aminopropanal tissue levels increased markedly within two hours after middle cerebral artery occlusion, and continued to increase further for at least 25 hr. Data shown are mean±s.d., n=3 animals/group. *$P<0.05$ vs t=0 hours by ANOVA.

Four closely related lines of evidence support the role of 3-aminopropanal as a cytotoxic mediator of cellular and tissue damage in cerebral ischemia. First, cerebral ischemia mediates an early induction of polyamine oxidase activity. Second, the cytotoxic enzyme product 3-aminopropanal accumulates during the early response to cerebral ischemia (FIG. 2), but is not a produced in normally perfused controls. Third, 3-aminopropanal production in the ischemic brain increases prior to the onset of significant cellular degeneration, with tissue 3-aminopropanal levels rising further during the period of progressive cell death. Fourth, 3-aminopropanal is a potent cytotoxin which activates apoptosis via an ICE-dependent mechanism in glial cells, and necrosis in neurons. Considered together, these data offer an explanation for the correlation between brain levels of putrescine, a stable end product of terminal polyamine oxidation, and infarct volume (Dempsey et al., *Neurosurg.* 17:635–640, 1985; Traynelis et al., *J. Physiol.* (*London*) 433:727–763, 1991; Gilad et al., *Mol. Chem. Neuropathol.* 18:197–210, 1993), since catabolism of spermine and spermidine by polyamine oxidase produces both a stable, non-toxic end product (putrescine) and a potent cytotoxin (3-aminopropanal). The latter product mediates cell death, and the former accumulates in correlation to the extent of damage.

Previous observations suggest that polyamines can prevent apoptosis in neuronal cultures (Harada and Sugimoto, *Brain Res* 753:251–259, 1997; and Xie et al., *Exp. Cell Res* 230:386–392, 1997), or amplify glutamate-mediated cell cytotoxicity (Pegg et al., *Biochem. Soc. Trans.* 22:846–852, 1994). Cell survival in the ischemic zone is likely to be critically dependent upon the balance between the direct effects of polyamines, and the cytotoxic effects of their metabolite, 3-aminopropanal. There has been some controversy as to whether both 3-aminopropanal and 3-acetamidopropanal can produce acrolein in vivo, a known mediator of cytotoxicity and apoptosis (Li et al., *Toxicol. Appl. Pharmacol.* 145:331–339, 1997; and Fernandez et al., *Br. J. Cancer* 72:1194–1199, 1995). Thus, it is likely that several products of polyamine oxidation could further augment the cytotoxicity of 3-aminopropanal. When considered together and without being bound by theory, these observations add further credence to the hypothesis that enhanced polyamine oxidation during ischemia is deleterious.

Without being bound by theory, these data suggest the following mechanism of brain cell death during cerebral ischemia: dead and dying cells in the densely hypoxic core release stores of intracellular spermine and spermidine, which is catabolized by polyamine oxidase. The resultant production of 3-aminopropanal causes apoptosis in surrounding glial cells, and necrosis of neurons, which in turn release more spermine and spermidine as substrate for polyamine oxidase. This cytotoxic mechanism spreads to involve a larger volume of potentially viable cells surrounding the ischemic core. It is likely that in concert with the excitatory amino acids, activated oxygen species, nitric oxide, TNF, IL-1, IL-6, and platelet-activating factor (Meistrell III et al., *SHOCK* 8:341–348, 1997; Zhang et al., *Stroke* 27:317–323, 1996; Coyle and Puttfarcken, *Science*

262:689–695,193; Rothwell and Strijbos, *Int J Dev. Neurosci* 13:179–185, 1995; Irikura et al., *Proc. Natl. Acad. Sci. USA* 92:6823–6827, 1995; Rothwell and Relton, *Cerebrovasc Brain Metab Rev* 5:178–198, 1993;Taupin et al., *J Neuroimmunol.* 42:177–185, 1993; Saito et al., *Neurosci Lett* 206:149–152, 1996; Choi, *J Neurobiol* 23:1261–1276, 1992; and Montague et al., *Science* 263:973–76, 1994), 3-aminopropanal is positioned as a proximal mediator in the cytoxicity cascade of cerebral ischemia Previous observations have noted that inhibition of ICE (IL-1β converting enzyme) protects against the development of apoptosis during cerebral ischemia (Friedlander et al., *J. Exp. Med.* 185:933–940, 1997; Gillardon etal., *Brain Res. Mol. Brain Res.* 50:16–22, 1997; and Hara et al., *J. Cereb. Blood Flow Metab.* 17:370–375, 1997). Since the stimulus to apoptosis during cerebral ischemia is unknown, it is reasonable to suggest a proximal role for 3-aminopropanal. Further, it was previously reported that TNF synthesis is upregulated during the first 12 hours of brain ischemia, which cytokine participates in the subsequent development of brain damage (Meistrell III et al., *SHOCK* 8:341–348, 1997). Spermine is a direct inhibitor of TNF synthesis in human peripheral blood mononuclear cells (Zhang et al., *J. Exp. Med.* 185:1–10, 1997). Moreover, the role of decreasing spermine levels during cerebral ischemia is unexplained and not reported.

Centrally administered 3-aminopropanal directly stimulated intracerebral TNF synthesis (data not illustrated in examples). These data provide additional evidence for a proximal role of 3-aminopropanal in the pathogenesis of stroke.

Early production and potent cytotoxicity of 3-aminopropanal define a proximal role of this aldehyde in the ischemic mediator cascade. Thus, polyamine oxidation contributes to cell cytotoxicity and these data do not contradict the potential role of other cytotoxic factors. Polyamines and polyamine oxidase are ubiquitous in all mammalian tissues (Seiler, *Biochimica et Biophysica Acta.* 615:480–488, 1980).

Table 1 provides a time course study of cell viability after exposure to 3-aminopropanal. Glial or neuronal cells were exposed to an $LD_{100}$ concentration of 3-aminopropanal (750 $\mu$M) for the times indicated, followed by replacing the media with fresh OPTI-MEM (medium) for a total incubation time of 20 hr. Cell viability was determined by MIT assay (data shown are mean±s.e).

|            | Cell Viability (% alive) | |
| --- | --- | --- |
| Time (min) | Glial cells (HTB14) | Neurons (HTB11) |
| 5    | 96 ± 3 | 29 ± 6 |
| 60   | 92 ± 1 | 13 ± 4 |
| 120  | 78 ± 7 | 6 ± 2 |
| 1200 | 5 ± 5  | 3 ± 1 |

These data support the notion that polyamine oxidase-derived 3-aminopropanal is a mediator of the brain damaging sequelae of cerebral ischemia, which can be therapeutically modulated. Brain polyamine oxidase activity was increased significantly within two hours after the onset of ischemia in brain homogenates (15.8±0.9 nmol/h/mg protein) as compared to homogenates prepared from the normally perfused contralateral side (7.4±0.5 nmol/h/mg protein) (P<0.05). The major catabolic products of polyamine oxidase are putrescine and 3-aminopropanal.

Although 3-aminopropanal is a potent cytotoxin, essential information was previously lacking on whether 3-aminopropanal is produced during cerebral ischemia. 3-aminopropanal accumulated in the ischemic brain within 2 hours after permanent forebrain ischermia in rats, but not in normally perfused brain.

Cytotoxic levels of 3-aminopropanal (750 $\mu$M) were achieved prior to the onset of significant cerebral cell damage, and increased in a time-dependent manner. Elevated 3-aminopropanal levels occurred in association with the development of progressive neuronal and glial cell death. Glial cell cultures that were exposed to 3-aminopropanal underwent apoptosis ($L.D._{50}$=275 $\mu$M) whereas neurons were killed by necrotic mechanisms ($L.D._{50}$=90 $\mu$M). The tetrapeptide ICE inhibitor (Ac-YVAD-CMK) prevented 3-aminopropanal-mediated apoptosis in glial cells. Finally, treatment of rats with two structurally distinct inhibitors of polyamine oxidase (aminoguanidine and chloroquine) attenuated brain polyamine oxidase activity, prevented the production of 3-aminopropanal, and significantly protected against the development of ischemic brain damage in vivo. Considered together, these results indicate that polyamine oxidase-derived 3-aminopropanal is a mediator of the brain damaging sequelae of cerebral ischemia, which can be therapeutically modulated.

Synthesis, Compounds and Formulations

The compounds of Formula I may have an asymmetric carbon atom which may occur in the R, $R_1$ and $R_3$ side-chains; optical isomers may likewise occur in the R, $R_1$ and $R_3$ side-chains of the compounds of Formula II. The isomers of a racemic mixture of any of these compounds can be separated by methods known to those skilled in the art and the isomeric preparations thus purified and isolated can be tested, by methods known to those skilled in the art or taught herein, to determine if such an isomeric preparation (as opposed to the corresponding racemic mixture) is more desirable, e.g., has less toxicity or greater potency, for use in the methods of this invention.

The compounds, compositions and treatment methods of this invention can be used to prevent or inhibit tissue necrosis and cell death in a variety of settings, particularly as the circumstances may be understood to involve the evolution of 3-aminopropanal and its role as a cytotoxin that propagates cellular damage. Such additional indications have in common the need to inhibit "innocent bystander" cell death. In other words, the compounds, compositions and methods of this invention find particular utility in preventing the spread of cell death outward from a fatally damaged, non-viable core into a potentially viable surrounding or penumbral zone. The initiating damage at the core may be due to any of a variety of causes (e.g., ischemia, embolism, thrombosis, hypoperfusion, injury, trauma, disease, heat, cold, chemical exposure, surgery, exposure to endogenous, environmental or therapeutic cytotoxins, radiation, necrosis, apoptosis, etc.); the compounds, compositions and methods of this invention will then find utility in preventing or limiting cellular damage and cell death in tissue adjacent to the non-viable core. Without accepting any limitation implied by mechanistic explanation, the compounds, compositions and methods of this invention are thought to operate in such diverse settings by molecular interference with and neutralization of the cytotoxic activity of 3-aminopropanal, which cytotoxin arises naturally from metabolism of polyamines released in the core and in the penumbra as cellular damage propagates outward from the initiating site. In each such instance, the compounds, compositions and methods of this invention may be usefully employed to limit tissue damage ancillary or adjacent to the site of initiating damage.

Compounds of formula I can be synthesized according to the following procedure. A general procedure for the synthesis of N-Phenyacyl Pyridinum Bromide derivatives: A solution of Pyridine (1.58 g, 20.0 mmol) and Bromoacetophenone (4.00 g, 20.0 mmol) in 50 ml of ethanol was refluxed for 6 h. The reaction progress was monitored by TLC using a mixture of ethyl acetate:methanol:water (4:2:1 and 1.0% of ammonia) as developing solvent. Upon cooling the reaction mixture, the product came out of solution as white precipitate which was filtered and recrystallized from ethanol as white needle crystal (MP. 216.4–220° C.) in 97% yield. Further characterizations of the new products were carried out using NMR and mass spectrometer.

Compounds according to formula 2 have been described, for example, in U.S. Pat. No. 5,656,261, the disclosure of which is incorporated by reference herein. Such compounds include, for example, 3-amino-thiazolium mesitylenesulfonate; 2,3-diamino-thiazolium mesitylenesulfonate; 3-(2-methoxy-2-oxoethyl)-4,5-dimethylthiazolium bromide; 3-(2-methoxy-2-oxoethyl)-4-methylthiazolium bromide; 3-(2-phenyl-2-oxoethyl)-4-methylthiazolium bromide; 3-(2-phenyl-2-oxoethyl)-4,5-dimethylthiazolium bromide; 3-amino4-methyl-thiazolium mesitylene sulfonate; 3-(2-methoxy-2-oxoethyl)-5-methyl-thiazolium bromide; 3-(2-phenyl-2-oxoethyl)-5-methyl-thiazolium bromide; 3-(2-[4$^1$-bromophenyl]-2-oxoethyl)-thiazolium bromide; 3-(2-[4$^1$-bromophenyl]-2-oxoethyl)-4-methyl-thiazolium bromide; 3-(2-[4$^1$-bromophenyl]-2-oxoethyl)-5-methyl-thiazolium bromide; 3-(2-[4$^1$-bromophenyl]-2-oxoethyl) -4,5-dimethylthiazolium bromide; 3-(2-methoxy-2-oxoethyl)-4-methyl-5-(2-hydroxyethyl)-thiazolium bromide; 3-(2-phenyl-2-oxoethyl)-4methyl-5-(2'-hydroxyethyl)-thiazolium bromide; 3-(2-[4$^1$-bromophenyl]-2-oxoethyl)-4-methyl-5-(2'-hydroxyethyl) thiazolium bromide; 3,4-dimethyl-5-(2-hydroxyethyl)-thiazolium iodide; 3-ethyl-5-(2-hydroxyethyl)-4-methyl thiazolium bromide; 3-benzyl-5-(2-hydroxyethyl))-4-methyl-thiazolium chloride; 3-(2-methoxy-2-oxoethyl)-benzothiazolium bromide; 3-(2-phenyl-2-oxoethyl)-benzothiazolium bromide; 3-(2-[4$^1$-bromophenyl)-2-oxoethyl)-benzo-thiazolium bromide; 3-(carboxymethyl)-benzothiazolium bromide; 2,3-diamino-benzothiazolium mesitylenesulfonate; 3-(2-amino-2-oxoethyl)-thiazolium bromide; 3-(2-amino-2-oxoethyl)-4-methyl-thiazolium bromide; 3-(2-amino-2-oxoethyl)-5-methyl-thiazolium bromide; 3-(2-amino-2-oxoethyl)-4,5-dimethyl-thiazolium bromide; 3-(2-amino-2-oxoethyl)-benzothiazolium bromide; 3-(2-amino-2-oxoethyl)-4-methyl-5-(2-hydroxyethyl) thiazolium bromide; 3-amino-5-(2-hydroxyethyl)-4-methyl-thiazolium mesitylenesulfonate; 3-(2-methyl-2-oxoethyl) thiazolium chloride; 3-amino-4-methyl-5-(2-acetoxyethyl) thiazolium mesitylenesulfonate; 3-(2-phenyl-2-oxoethyl) thiazolium bromide; 3-(2-methoxy-2-oxoethyl)-4-methyl-5-(2-acetoxyethyl) thiazolium bromide; 3-(2-amino-2-oxoethyl)-4-methyl-5-(2-acetoxyethyl) thiazolium bromide; 2-amino-3-(2-methoxy-2-oxoethyl) thiazolium bromide; 2-amino-3-(2-methoxy-2-oxoethyl) benzothiazolium bromide; 2-amino-3-(2-amino-2-oxoethyl) thiazolium bromide; 2-amino-3-(2-amino-2-oxoethyl) benzothiazolium bromide; 3-[2-(4'-methoxyphenyl)-2-oxoethyl]-thiazolinium bromide; 3-[2-(2',4'-dimethoxyphenyl)-2-oxoethyl]-thiaxolinium bromide; 3-[2-(4'-fluorophenyl)-2-oxoethyl]-thiazolinium bromide; 3-[2-(2',4'-difluorophenyl)-2-oxoethyl]-thiazolinium bromide; 3-[2-(4'-diethylaminophenyl)-2-oxoethyl]-thiazolinium bromide; 3-propargyl-thiazolium bromide; 3-propargyl-4-methyl thiazolium bromide; 3-propargyl-5-methyl thiazolium bromide; 3-propargyl-4, 5-dimethyl thiazolium bromide; 3-propargyl-4-methyl-5-(2-hydroxyethyl)-thiazolium bromide; 3-(2-[3'-methoxyphenyl]-2-oxoethyl)-thiazolium bromide; 3-(2-[3'-methoxy phenyl]-2-oxoethyl)-4methyl-5-(2'-hydroxyethyl)-thiazolium bromide; 3-(2-[3'-methoxyphenyl]-2-oxoethyl-benzothiazolium bromide; 2,3-diamino-4-chlorobenzothiazolium mesitylenesulfonate; 2,3-diamino-4-methyl-thiazolium mesitylene sulfonate; 3-amino-4-methyl-5-vinyl-thiazolium mesitylene sulfonate; 2,3-diamino-6-chlorobenzothiazolium mesitylenesulfonate; 2,6-diamino-benzothiazole dihydrochloride; 2,6-diamino-3 [2-(4'-methoxyphenyl)-2-oxoethyl]benzothiazolium bromide; 2,6-diamino-3 [2-(3'-methoxyphenyl)-2-oxoethyl] benzothiazolium bromide; 2,6-diamino-3 [2-(4'-diethylaminophenyl)-2-oxoethyl]benzothiazolium bromide; 2,6-diamino-3 [2-(4'-bromophenyl)-2-oxoethyl] benzothiazolium bromide; 2,6-diamino-3 (2-(2-phenyl-2-oxoethyl) benzothiazolium bromide; 2,6-diamino-3 [2-(4'-fluorophenyl-2-oxoethyl]benzothiazolium bromide; 3-acetamido-4-methyl-5-thiazolyl-ethyl acetate mesitylenesulfonate; 2,3-diamino-5-methylthiazolium mesitylenesulfonate; 3-[2-(2'-naphthyl)-2-oxoethyl]-4-methyl-5-(2'-hydroxyethyl)-thiazolium bromide; 3-[2-(3',5'-Di-tert-butyl-4'-hydroxyphenyl)-2-oxoethyl[-4-methyl-5-(2'-hydroxyethyl)-thiazolium bromide; 3-[2-(2',6'-Dichlorophenethylamino)-2-oxoethyl]-4-methyl-5-(2'-hydroxyethyl)-thiazolium-bromide; 3'[2-Dibutylamino-2-oxoethyl]-4-methyl-5-(2'-hydroxyethyl)-thiazolium bromide; 3-[2-4'-carbethoxyanilino)-2-oxoethyl]-4-methyl-5-(2'-hydroxyethyl)-thiazolium bromide; 3-[2-(2',6'-Diisopropylanilino)-2-oxoethyl]-4-methyl-5-(2'-hydroxyethyl)-thiazolium bromide; 3-amino-4-methyl-5-[2 (2',6'-dichlorobenzyloxy) ethyl]-thioazolium mesitylenesulfonate; 3-[2-(4'-carbmethoxy-3'-hydroxyanilino)-2-oxoethyl]-4-methyl-5-(2'-hydroxyethyl)-thiazolium bromide; 2,3-Diamino-4,5-dimethyl thiazolium mesitylene sulfonate; 2,3-Diamino-4-methyl-5-hydroxyethyl-thiazolium mesitylene sulfonate; 2,3-Diamino-5-(3',4'-trimethylenedioxy phenyl) thiazolium mesitylene sulfonate; 3[2-(1',4'-benzodioxan-6-yl)-2-oxoethyl]-4-methyl-5-(2'-hydroxyethyl-thiazolium bromide; 3'[2-(3',4'-trimethylenedioxyphenyl)-2-oxoethyl]-4-methyl-5-(2-hydroxyethyl)-thiazolium bromide; 3-(2-[1',4-benzodioxan-6-yl]-2-oxoethyl)-thiazolium bromide; 3-[2-(3',4'-trimethylenedioxyphenyl)-2-oxoethyl]-thiazolium bromide; 3-[2-(3',5'-di-tert-butyl-4'-hydroxyphenyl)-2-oxoethyl]-thiazoliun bromide; 3-[2-(3',5'-di-tert-butyl-4'-hydroxyphenyl)-2-oxoethyl]-4-methyl-thiazolium bromide; 3-[2-(3',5'-di-tert-butyl-4'-hydroxyphenyl)-2-oxoethyl]-5-methyl-thiazolium bromide; 3-[2-(3',5'-di-tert-butyl-4'-hydroxyphenyl)-2-oxoethyl]-4,5-dimethyl-thiazolium bromide; 3-[2-(3',5'-di-tert-butyl-4'-hydroxyphenyl)-2-oxoethyl-[benzothiazolium bromide; 1-methyl-3-[2-(3',5'-di-tert-butyl-4'-hydroxyphenyl)-2-oxoethyl]-imidazolium bromide; 3-[2-(4'-n-pentylphenyl)-2-oxoethyl]-thiazolinium bromide; 3-[2-(4'-n-pentylphenyl)-2-oxoethyl]-4-methyl-5-(2'-hydroxyethyl)-thiazolinium bromide; 3-[2-4'-diethylaminophenyl)-2-oxoethyl]-4-methyl-5-(2'-hydroxyethyl)-thiazolinium bromide; 3-(2-phenyl-2-oxoethyl)-4-methyl-5-vinyl-thiazolium bromide; 3-[2-(3',5'-tert-butyl-4'-hydroxyphenyl)-2-oxoethyl)-4-methyl-5-vinyl-thiazolium bromide; 3-(2-tert-butyl-2-oxoethyl) -thiazolium bromide; 3-(2-tert-butyl-2-oxoethyl)-4-methyl-5-(2'-hydroxyethyl)-thiazolium bromide; 3-(3'-methoxybenzyl)-4-methyl-5-(2'-hydroxyethyl)-thiazolium chloride; 3-(2',6'-dichlorobenzyl)-4-methyl-5-(2'-hydroxyethyl)-thiazolium chloride; 3-(2'-nitrobenzyl)-4-methyl-5-(2'-hydroxyethyl)-thiazolium bromide; 3 [2-(4'-chlorophenyl)-2-oxoethyl]-thiazolium bromide; 3 [2-(4'-chlorophenyl)-2-oxoethyl]-4-methyl-5-(2'-hydroxyethyl)-thiazolium bromide; and 3 [2-(4'-methoxyphenyl)-2-oxoethyl]-4-methyl-5-(2'-hydroxyethyl)-thiazolium bromide.

Therapeutic Uses, Routes of Administration and Formulations

The present invention provides novel compounds, pharmaceutical formulations and methods of treatment to mitigate ischemic damage. Effective doses of the therapy, as described below, may be formulated in suitable pharmacological carriers and may be administered by any appropriate means, including, but not limited to injection (intravenous, intraperitoneal, intramuscular, intracranial, intramyocardial, subcutaneous), by absorption through epithelial or mucocutaneous linings (oral mucosa, rectal and vaginal epithelial linings, nasopharyngeal mucosa, intestinal mucosa); orally, transdermally or any other means available within the pharmaceutical arts.

A compound can be administered to a human patient by itself or in pharmaceutical compositions where it is mixed with suitable carriers or excipients at doses to treat or mitigate tissue ischemia or to mitigate ischemic damage. Preferably, the organ sites of treatment are the CNS and the myocardium. A therapeutically effective dose further refers to that amount of the compound sufficient to treat or mitigate tissue ischemia or to mitigate ischemic damage. Therapeutically effective doses may be administered alone or as adjunctive therapy in combination with other treatments for tissue ischemia or to mitigate tissue ischemic damage. Techniques for the formulation and administration of the compounds of the instant application may be found in "Remington's Pharmaceutical Sciences" Mack Publishing Co., Easton, Pa., latest addition.

Suitable routes of administration may, for example, include oral, rectal, transmucosal, or intestinal administration; parenteral delivery, including intramuscular, subcutaneous, intracranial, intrascerebroventricular, intramedullary injections, as well as intrathecal, direct intraventricular, intravenous, intraperitoneal, intranasal, or intraocular injections, and optionally in a depot or sustained release formulation.

Furthermore, one may administer the agent of the present invention in a targeted drug delivery system, for example in a liposome coated with a tissue-targeting antibody. The liposomes will be targeted to and taken up selectively by target tissue cells.

The pharmaceutical compositions may be manufactured by means of conventional mixing, dissolving, dragee-making, levitating, emulsifying, encapsulating, entrapping, or lyophilizing processes. Pharmaceutical compositions for use in accordance with the invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers, such as Hank's solution, Ringer's solution, or physiological saline buffer. For transmucosal administration, penetrants appropriate to the barrier to be permeated are used in the formulation. Such penetrants are usually known in the art.

For oral administration, the compounds can be formulated by combining the active compounds with pharmaceutically acceptable carriers. Such carriers enable the compounds to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner. For administration by inhalation, the compounds for use according to the invention are delivered in the form of an aerosol spray presentation from pressurized packs or a nebulizer, with the use of a suitable propellant, such as, dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

The compounds may be formulated for parenteral administration by injection, such as, by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulary agents such as suspending, stabilizing and/or dispersing agents.

Pharmaceutical formulations for parenteral administration include, for instance, aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle before injection, such as, sterile pyrogen-free water.

Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds described herein and identified as useful for treating or mitigating tissue ischemia or mitigating ischemic damage may be provided as salts with pharmaceutically compatible counterions. Pharmaceutically compatible salts may be formed with many acids, including but not limited to hydrochloric, sulfuric, acetic, lactic, tartaric, malic, succinic, etc.; or bases. Salts tend to be more soluble in aqueous or other protonic solvents that are the corresponding free base forms. Examples of pharmaceutically acceptable salts, carriers or excipients are well known to those skilled in the art and can be found, for example, in *Remington's Pharmaceutical Sciences,* 18th Edition, A. R. Gennaro, Ed., Mack Publishing Co., Easton, Pa., 1990. Such salts include, but are not limited to, sodium, potassium, lithium, calcium, magnesium, iron, zinc, hydrochloride, hydrobromide, hydroiodide, acetate, citrate, tartrate, malate salts, and the like.

Pharmaceutical compositions suitable for use in the present invention include compositions wherein the active ingredients are contained in an effective amount to achieve their intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. In addition, therapeutically useful doses from in vivo experiments are provided with the in vivo data of preferred embodiments illustrated herein. Such information can be used to more accurately determine useful doses in humans.

A therapeutically effective dose refers to that amount of the compound that results in a reduction in the otherwise expected severity of stroke of damage in a prolongation of survival in a patient. Toxicity and therapeutic efficacy of such compounds can be determined by standard pharmaceutical, pharmacological, and toxicological procedures in cell cultures or experimental animals for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from cell culture assays or animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

Dosage amount and interval may be adjusted individually to provide plasma levels of the active moiety which are sufficient to maintain the desired modulating effects, or minimal effective concentration (MEC). The MEC will vary for each compound but can be estimated from in vitro data; such as, the concentration necessary to achieve a 50–90% inhibition of polyamine-derived or 3-aminopropanal-mediated cellular damage (in vitro) or achieve a reduction in the otherwise expected severity of stroke or ischemic damage in vivo using the assays described herein. Dosages necessary to achieve the MEC will depend on individual characteristics and route of administration. However, HPLC assays, bioassays or immunoassays can be used to determine plasma concentrations.

The amount of composition administered will be dependent on the subject being treated, on the subjects weight, the severity of the affliction, the manner of administration and the judgment of the prescribing physician.

Screening Assays

The present invention further provides an in vivo screening assay comprising administering a polyamine compound or 3-aminopropanal into the brain parenchyma of a test animal by microinjection, administering a test compound or control agent locally or systemicly, and measuring cortical cytotoxicity in stained brain sections from the test animals generated by the location of microinjection. Preferably, the polyamine compound is spermine or spermidine or metabolites thereof. Preferably, the test animal is a rat. Preferably, cytotoxicity of stained brain sections is measured by planimetric analysis. Example 2 below provides an experiment using this in vivo assay procedure and demonstrates cytotoxic activity of 3-aminopropanal, spermine and spermidine but not putrescine. The model was verified by systemic administration of polyamine oxidase inhibitors chloroquine and aminoguanidine.

The present invention further provides an in vitro screening assay comprising exposing cultured glial cells or neuronal cells related cell lines to 3-aminopropanal at a concentration of from about 50 to about 1000 $\mu M$, adding various concentrations of test compound or control media to the cell cultures, incubated under cell culture conditions for a period of from about 5 minutes to about 20 hours, and determining the percentage of cell viability. Preferably, the concentration of 3-aminopropanal in the cell culture medium is approximately 80 $\mu M$. Preferably, the method for determining cell viability is by measuring metabolically-dependent reduction of 3-(4,5-dimethylthiazol-2-yl)-2,5-diphenyltetrazolium (MTT). Another method for determining cell death is by looking for evidence of apoptosis, for examply by a terminal doxynucleotidyl transferase mediated dUTP nick end labeling (TUNEL) method (Gavrieli et al., *J. Cell. Bio.* 119:493–501, 1992). Example 3 below provides additional working details for the in vitro screening assay, and Example 5 below shows exemplary assay results with a variety of test compounds.

EXAMPLE 1

3-Aminopropanal Mediates Tissue Damage Resulting from Ischemia

Polyamine Oxidase Activity is Increased Following Ischemia

To determine the role of polyamine oxidase activity and the metabolites it generates from polyamines in the tissue damage attendant to ischemia, an animal model of stroke was conducted. Lewis rats were subjected to focal cerebral ischemia by microsurgical occlusion of the middle cerebral artery in a standardized model as described previously (Zimmerman et al., *Proc. Natl. Acad. Sci. USA* 92:3744–3748, 1995; Cockroft et al., *Stroke* 27:1393–1398, 1996; and Meistrell III et al., *SHOCK* 8:341–348, 1997). Briefly, the ipsilateral common carotid artery was ligated and divided, the middle cerebral artery coagulated and divided distal to the lenticulostriate branch, and the contralateral common carotid temporarily occluded for 1 hr. The onset of ischemia in these experiments was defined as the time the middle cerebral artery was cut. For measurement of infarct volume, the animals were euthanized at the time indicated and fresh brain sections prepared (1 mm), immersed in 2,3,5-triphenyltetrazolium chloride (TTC) in 154 mM NaCl for 30 min at 37° C., and total cerebral infarct volume measured by computerized quantitative planimetry as described elsewhere (Zimmerman et al., *Proc. Natl. Acad Sci. USA* 92:3744–3748, 1995; Cockroft et al., *Stroke* 27:1393–1398, 1996; and Bederson et al., *Experientia* 41:1209–1211, 1986). Similar measurements of stroke volume (infarct size) were obtained in separate experiments using planimetric analysis of brain sections stained with hematoxylin and eosin. All procedures involving animals in this example and in the following examples were conducted in conformity with institutional guidelines and under the approval of the Animal Care and Use Comminee of North Shore University Hospital-New York University Medical School.

To measure tissue polyamine oxidase activity, brain homogenates were prepared from the anatomic region perfused by the middle cerebral artery, and total polyamine oxidase activity determined using a method described previously (Seiler and Bolkenius, *Neurochem. Res.* 10:529–544, 1985; Seiler et al., *Med. Biol.* 59:334–346, 198 1; and Milani et al., *J. Neurosci. Res.* 28:434–441, 1991), relying on the metabolic conversion of added spermine. Briefly, two hours after permanent occlusion of the middle cerebral artery, a 4 mm thick coronal section of the ipsilateral hemisphere encompassing the zone of ischemia (beginning 3 mm caudal from the frontal pole) was manually homogenized on ice in 1.5 ml of Hanks media containing 1 mM phenylmethylsulfonyl fluoride (PMSF) and centrifuged at 43,000×g for 30 min. Brain polyamine oxidase activity in the resultant homogenate supernatant was determined by addition of spermine at time zero (50 $\mu$l of a 1 mM stock solution added per 1 ml of homogenate supernatant). For experiments using enzyme inhibitors, aminoguanidine or chloroquine in the pharmacological concentration range (50 $\mu$M–5 mM) was added 5 minutes prior to spermine. The spermine-containing supernatants were maintained at 37° C., and at time points up to 60 min after the addition of spermine, duplicate 200 $\mu$l samples were removed and enzyme activity was stopped by addition of 10 $\mu$l of 60% perchloric acid (PCA). Samples for HPLC analysis to detect spermine were prepared with dansyl chloride (200 $\mu$l of 10 mg/ml dansyl chloride solution in acetone and 200 $\mu$l saturated aqueous $Na_2CO_3$ per 50 $\mu$l sample homogenate supernatant; 10 min incubation at 65° C.; brief centrifugation to clear) and dansylated spermine was detected by fluoresence after fractionation by HPLC (20 $\mu$l injectate; Vydac analytical C4 column eluted in a linear gradient from 0–100% methanol (in $H_2O$) over 35 min). Enzyme activity was corrected for the protein content of the homogenate supernatants, and data expressed as mean±s.d.; n=3 brain homogenates per condition.

Figure 1:
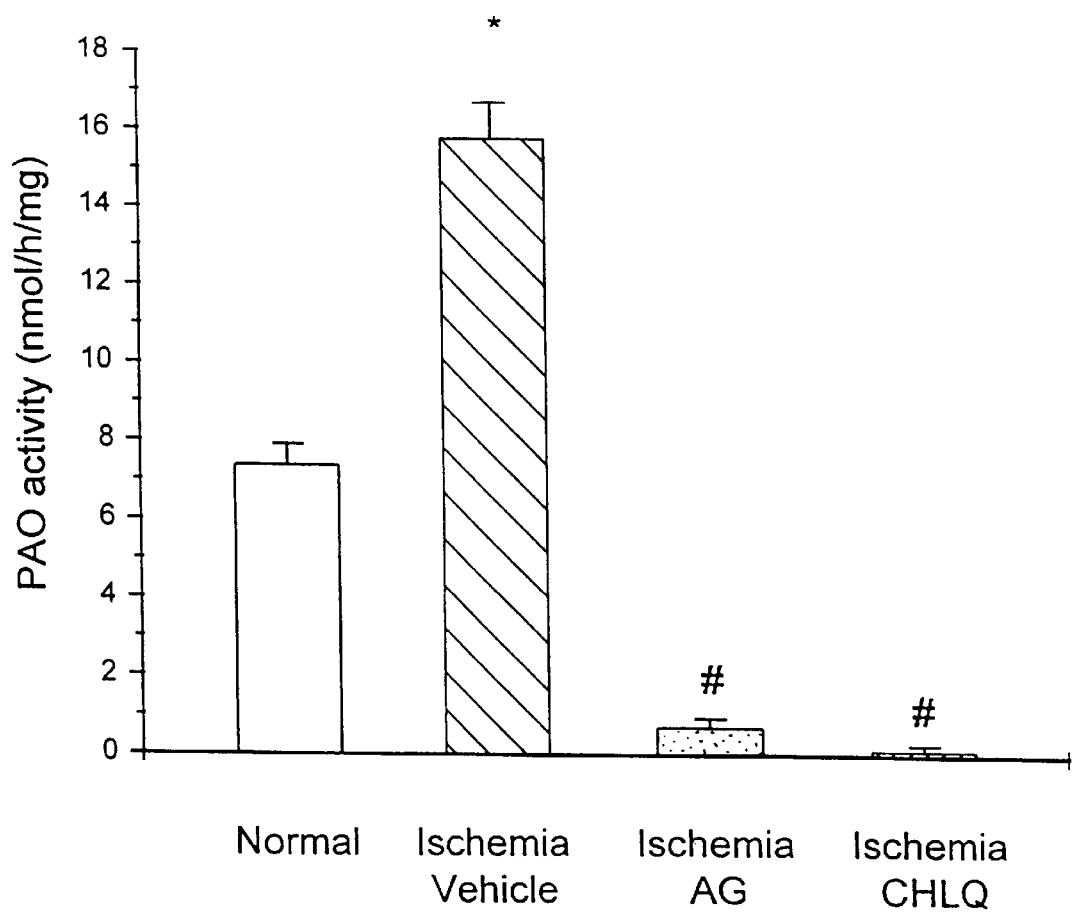
FIG. 1 shows that polyamine oxidase activity increased during cerebral ischemia, and was inhibited by aminoguanidine and chloroquine. Polyamine oxidase activity was measured in brain homogenates. Data shown are mean±s.d.; n=3. "Normal"=sham operated control brain homogenate; "Ischemia Vehicle"=homogenate prepared 2 hr after the onset of middle cerebral artery occlusion; "Ischemia AG"= addition of aminoguanidine (1 mM) at time=−5 minutes prior to spermine; and "Ischemia CHLQ"=addition of chloroquine (1 mM) at time=−5 minutes prior to spermine. *$P<0.05$ vs Normal; #$P<0.05$ vs Ischemia Vehicle.

Polyamine oxidase activity was significantly higher in homogenates prepared from ischemic hemispheres as compared to the contralateral (control) hemispheres (PAO activity after ischemia=15.8±0.9/h/mg protein vs. PAO activity in contralateral controls=7.4±0.5 nmol/h/mg protein, P<0.05; see FIG. 1). This increase in brain polyamine oxidase activity was detected as early as 2 hours after the onset of cerebral ischemia, suggesting that enhanced PAO activity occurred as part of the earliest response to ischemia Two known, structurally distinct inhibitors of polyamine oxidase activity, aminoguanidine and chloroquine (Seiler et al., *Med. Biol.* 59:334–346, 1981; Holtta, *Biochem.* 16:91–100, 1977; Flayeh, *Clin. Chem.* 34:401403, 1988; and Gahl and Pitot, *Biochem. J.* 202:603–611, 1982), were selected to determine the specificity of this spermine-metabolizing activity. Addition of either of these agents to homogenates of ischemic brain dose-dependently inhibited polyamine oxidase activity (see FIG. 1); chloroquine $I.C._{50}$= 40 $\mu$M; aminoguanidine $I.C._{50}$=400 $\mu$M. These data indicate that within 2 hours after the onset of cerebral ischemia there is a specific induction of brain polyamine oxidase activity, and that this activity is susceptible to inhibition by known inhibitors of polyamine oxidase.

3-Aminopropanal Levels are Increased Following Ischemia

To determine whether the increase in brain PAO activity associated with focal cerebral ischemia causes enhanced 3-aminopropanal production, a method to detect 3-aminopropanal in tissue samples was developed. To develop the method, 3-aminopropanal was prepared by hydrolysis of the diethyl acetal and then derivatized using 2,4-dinitrophenylhydrazine. Specifically, 3-aminopropanal was prepared by hydrolysis of 145 mM 3-aminopropanal diethyl acetal (TCI America) in 1.5 M HCl for 5 hours at room temperature. The reaction mixture was applied to a column (3 cm×6 cm) of Dowex-50 (H+-form) ion exchange resin and eluted with a step gradient of 0–3 M HCl (160 ml; flow rate 0.7 ml/min). Fractions containing aldehyde, as determined by the method of Bachrach and Reches (Bachrach and Reches, *Anal. Biochem.* 17:38–48, 1966), were concentrated in a centrifugal evaporator at room temperature. The concentration of aldehyde (i.e., 3-aminopropanal) was determined spectrophotometrically at 531 nm, based on a reaction of aldehydes with 4-amino-3-hydrazino-5-mercapto-1,2,4-triazole ('Purpald'; Aldrich) (Dickinson and Jacobsen, *Chemical Communications* 1719–720, 1970) with reference to a standard curve using propionaldehyde (Sigma). Acidic solutions of the aldehyde were neutralized with NaOH to physiological pH immediately before use. Vehicle control solutions were prepared, consisting of the same stoichiometric amounts of HCl and NaOH.

To derivatize 3-aminopropanal, 2,4-dinitrophenylhydrazine (2,4-DNPH; 0.5 g of 2,4-DNPH dissolved in 11 ml of concentrated HCl/ethanol (1:10, v/v)) was refluxed for 10 seconds with aqueous 3-aminopropanal.

The resulting 3-aminopropionaldehyde-2,4-dinitrophenylhydrazone derivative (3-AP-2,4-DNPH) was precipitated at room temperature, and collected by filtration. $^1$H-NMR spectrometry (DMSO-$d_6$ and $CDCl_3$, 270 MHz) of purified 2,4-dinitrophenylhydrazone derivative was employed to confirm its structure. The NMR spectrum revealed the presence of syn and anti isomers (1:1) with resonance at $\delta 8.83$ and $\delta 11.35$. A standard curve was generated by an HPLC assay of the dansylated derivative of the compound (see below).

An additional standard curve was constructed to quantify recovery of derivatized 3-aminopropanal from tissue homogenates. Briefly, a 4 mm thick brain slice obtained from the region perfused by the middle cerebral artery was homogenized manually, followed by addition of 3-aminopropanal (at 100, 150, 200, 300, 1000 nmol/ml) and 1.5 ml of 2,4-DNPH reagent. The samples were refluxed in the presence of the 2,4-DNPH reagent for 10 seconds, then 20 μl of 60% perchloric acid (PCA) was added to stop the reaction, followed by 200 μl of water. The samples were vigorously vortexed, centrifuged at 14,000 rpm for 30 min, and the supernatant concentrated to near dryness in a centrifugal evaporator. Samples were redissolved in 100 μl of water, centrifuged for 10 min at 14,000 rpm to clear precipitates, then prepared for assay by HPLC.

An HPLC detection system was used for detection of the derivatization products of 3-aminopropanal and 2,4-dinitrophenylhydrazine as follows. A Hewlett-Packard Model 1090 liquid chromatograph (Wilmington, Del., USA) equipped with an autosampler, photo diode-array and fluorescence detectors, and Chemstation operating software was used for all analyses. Detection by fluorescence was used, based on the reaction of 5-dimethyl-aminonapthalene sulfonyl-chloride (Dansyl chloride; Molecular Probes; relative fluorescence at 340 nm with excitation at 430 nm) with primary and secondary amines. Dansylation was performed by reacting 50 μl of the sample with 200 μl of 10 mg/ml dansyl chloride solution in acetone, 200 μl of saturated $Na_2CO_3$ solution, 3 μl 60% PCA and 3 μl mM 1,7-diaminoheptane (Sigma), followed by incubation at 65° C. for 10 min. 20 μl of the resulting derivatized sample was injected onto a Vydac C-4 250×4.6 mm column with 5 mm particle size. Using a flow rate of 1.0 ml/min, runs were initiated at 100% A ($dH_2O$) and a linear gradient to 100% B (methanol) was performed over 45 min., followed by 5 min. of 100% B and a return to 100% A over 5 min.

HPLC analysis of the 2,4-DNPH-derivatized, dansylated products revealed two peaks (24 min and 27 min) in equal ratio, attributable to the geometric isomers shown below (without dansylation):

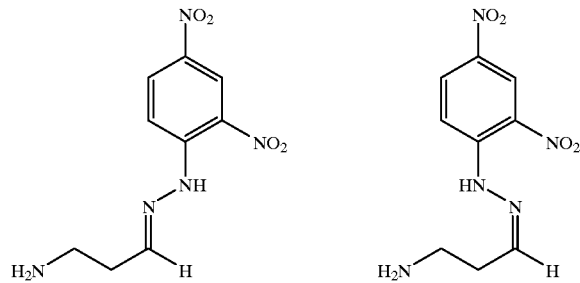

Electrospray ionization mass spectroscopy (EIMS) of the HPLC-purified products conformed to the expected mass ion, m/z 251, for the non-dansylated isomers.

Brain homogenates were prepared as above after 2 hours or 25 hours of ischemia from rats subjected to Permanent focal cerebral ischemia, and the homogenates were derivatized with 2,4-dinitrophenylhydrazine as above. HPLC analysis of the dansylated derivatized homogenates revealed the appearance of two peaks, and EIMS confirmed their identities as the isomeric 3-aminopropanal-2,4-dinitrophenylhydrazine reaction products. The 3-aminopropanal derivatization products were not detected by this HPLC-based assay in brain homogenates prepared from sham-operated, normally perfused control animals, indicating that ischemia mediated the appearance of 3-aminopropanal.

Thus, use of the quantitative HPLC-based assay for derivatized 3-AP (described above), which can reproducibly detect 1–2 μM 3-aminopropanal in brain tissue, confirmed that 3-aminopropanal is not present or produced in homogenates prepared from normally perfused brain. However, within 2 hours after the onset of cerebral ischemia, it was observed that there were significantly increased 3-aminopropanal levels, which increased further in a time-dependent manner for a least 25 hr after the onset of ischemia (see FIG. 2; results are expressed following normalization for protein content as measured by the Bradford method (Biorad), and after correction for HPLC injection volume using an internal standard of 1,7-diaminoheptane. Data are mean±s.d.; n=3–4 animals per group). When considered with the foregoing observation that cerebral ischemia mediates an early induction of brain polyamine oxidase activity, these findings indicate that ischemia induces PAO activity which produces 3-AP as a metabolite, and that this enzyme pathway continues to generate 3-aminopropanal during at least the first day after the onset of cerebral ischemia.

The HPLC assay employed may well have underestimated the amount of 3-aminopropanal produced in the ischemic brain, because 3-aminopropanal is a reactive molecule which can bind to the amino and sulfhydryl groups of proteins (Brunton et al., *Toxic. In Vitro* 8:337–341, 1994; and Seiler, *Digestion* 46:319–330, 1990), thereby decreasing its availability for derivatization and detection. Nonetheless, after correcting the measured levels for total brain protein (213 g/kg), brain 3-aminopropanal concentrations after ischemia reached a highly cytotoxic range (0.75 to 2.0 mM).

A further set of experiments was conducted to examine the time course of 3-aminopropanal production relative to the development of brain cell death. These experiments were necessary in order to determine whether the enzymatic formation of 3-aminopropanal was temporally upstream of the onset of brain cell death. Accordingly, the volume of cell death was measured by preparing sections from ischemic brain, staining with the vital dye, 2,3,5-triphenyltetrazolium chloride (TTC), and integrating the total area of dead tissue across multiple sections. For the first three hours of ischemia, cells in the region of the occluded middle cerebral artery were observed to be largely viable (total volume of cell death=2±2 mm$^3$). Histological examination of hematoxylin and eosin-stained brain sections confirmed that cells were morphologically intact and had not yet developed degenerative changes at a time when 3-aminopropanal levels were already significantly increased. Over the subsequent 25 hours, it was observed that the volume of brain cell death "spread" to involve a significantly larger region (infarct volume at 25 hours=71±24 mm$^3$; vs infarct volume at 3 hours=2±2 mm$^3$; P<0.05), and this "spreading" cell death developed in association with increasing 3-aminopropanal levels. These findings give evidence that significant accumulation of 3-aminopropanal occurs during the early response to cerebral ischemia, and precedes the development of overt, progressive brain cell death.

EXAMPLE 2

In vivo Screening Assay for Agents that Inhibit 3-aminopropanal-mediated Tissue Damage Exogenous 3-aminopropanal, or Polyamines Metabolizable to Yield 3-aminopropanal, Cause Brain Damage in vivo Since polyamine oxidase activity is present in normal mammalian brain (Paschen, *Cerebrovasc. Brain Metab. Rev.* 4:59–88, 1992; and Seiler and Bolkenius, *Neurochem. Res.* 10:529–544, 1985), the next experiment investigated whether increased extracellular levels of substrate (e.g., spermine or spermidine) would stimulate the production of 3-aminopropanal and induce local cell death. To investigate this possibility, spermine, spermidine, and metabolites thereof were administered into the cerebral cortex of rats by direct stereotactic microinjection, and the brain volume of resulting cell death measured by TTC staining brain sections. Polyamines or 3-aminopropanal were administered into rat brain cortex in vivo by stereotactically-guided microinjection into a location selected to correspond to the stereotactic/anatomic co-ordinates perfused by the middle cerebral artery. Briefly, male Lewis rats (270–300 g) were anesthetized and placed in a stereotactic head frame (Stoelting Co., Wood Dale, Ill., USA). The incisor bar was adjusted until the plane defined by the lambda and bregma was parallel to the base plate. A microsurgical craniotomy was performed 1.7 mm anterior to bregma, and 5 mm right of the midline, and the tip of a 29-gauge needle advanced 2 mm deep to the dural opening. Polyamine-containing solution (25 $\mu$g/2 $\mu$l) prepared in sterile saline (NaCl, 154 mM) was injected over 3 minutes, the needle then left undisturbed for 5 minutes, then removed. Animals were euthanized 48 hr later, the brains excised and sectioned in 1 mm thick slices in the coronal plane, and the sections immersed for 30 minutes at 37° C. in a solution containing 2,3,5-triphenyl-2H-tetrazolium chloride (2% in NaCl, 154 mM). Brain infarction was visualized as areas of unstained (white) tissue which were easily contrasted against viable tissue, which stained red. Slices were placed in buffered 10% formalin and infarct size quantitatively assessed by planimetric analysis. In separate studies, histopathological analysis of brain sections verified the location of the injectate and the correlation of tissue damage revealed by TTC staining. Groups of 3–4 animals were used for each of the experimental conditions as noted.

Figure 3:
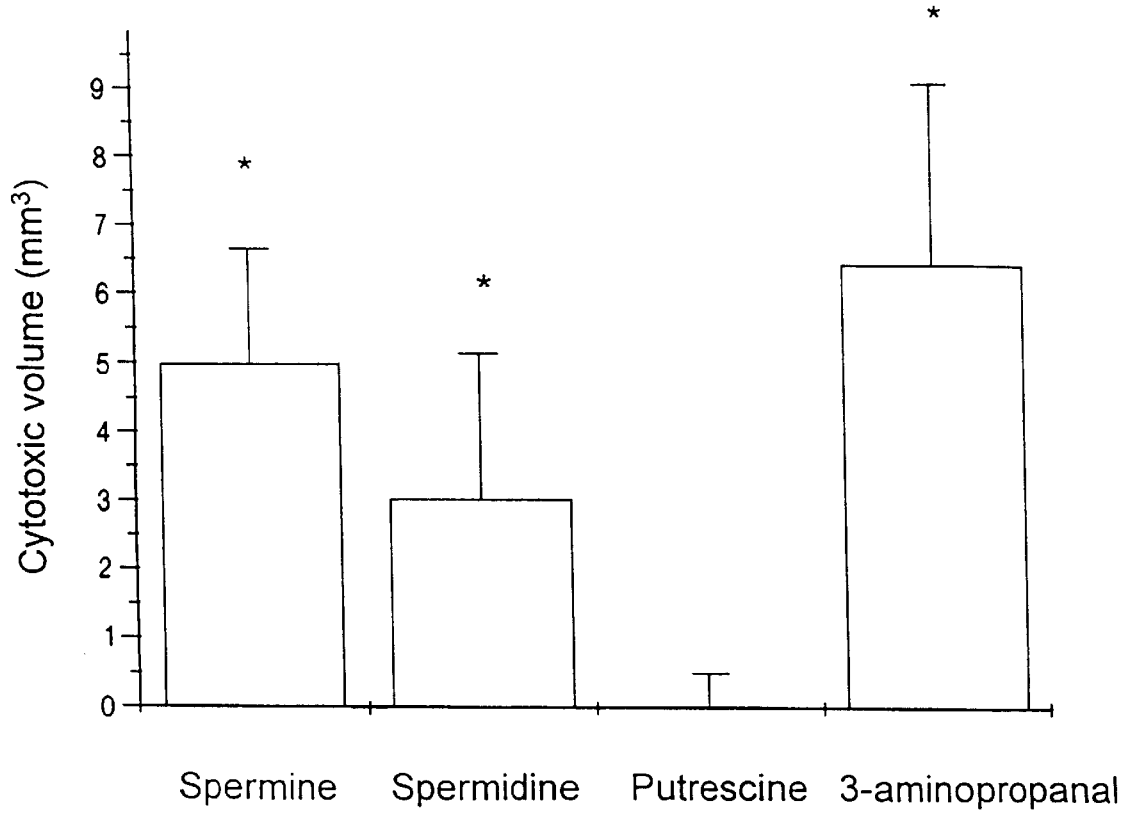
FIG. 3 shows the brain-damaging effects of intracortically administered polyamines and a metabolite thereof, 3-aminopropanal. Brain damage (infarct or cytotoxic volume) was measured after intracortical microinjection of spermine, spermidine, 3-aminopropanal and putrescine. Data shown are volume of brain damage ($mm^3$) as measured by integrating the area of negative TTC staining over the entire brain hemisphere in animals injected with the polyamines shown; mean±s.e.m., n=6–8/group. *P<0.05 vs vehicle. Of note, putrescine did not cause tissue damage; polyamine substrates metabolized by PAO to yield 3-aminopropanal, or 3-aminopropanal itself, were brain damaging.
Figure 4:
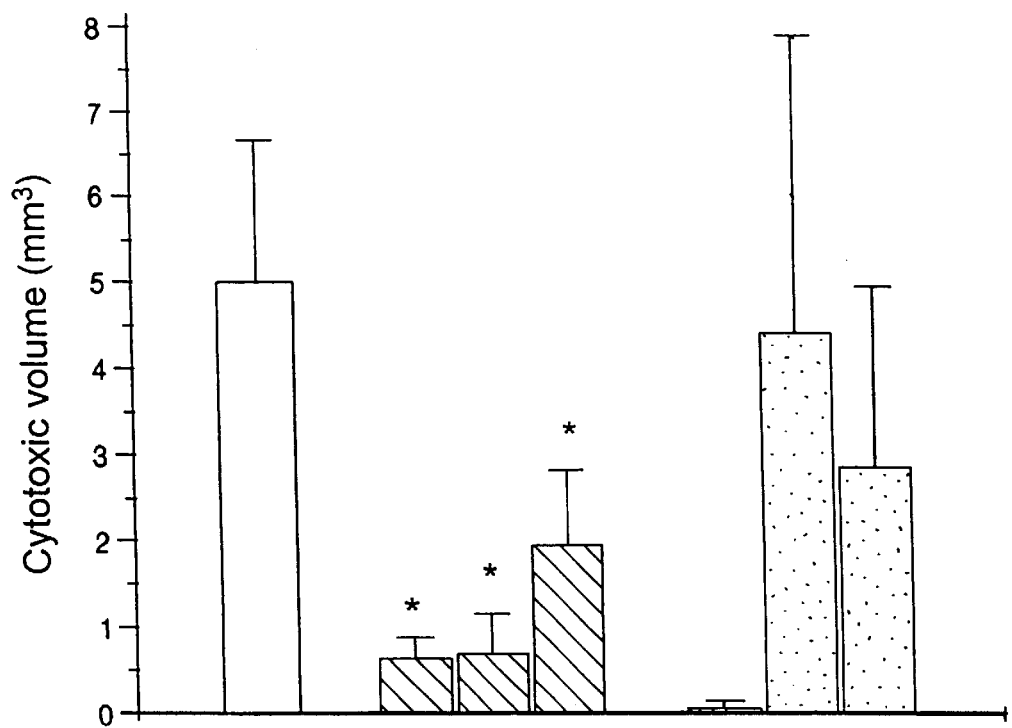
FIG. 4 shows that aminoguanidine and chloroquine protected against intracortical spermine toxicity. All animals received intracortical spermine (25 µg in 2 µl) by stereotactically-guided microinjection as described infra. Experimental animals were treated with aminoguanidine or chloroquine in connection with the intracortical spermine according to the following dose schedules: systemic aminoguanidine was 320 mg/kg, i.p. 30 minute pretreatment followed by subsequent doses of 110 mg/kg i.p. each 8 hr after intracortical spermine; intracortical aminoguanidine was a single dose (320 mg/kg) simultaneously with intracortical spermine; chloroquine was a single intraperitoneal dose (25 mg/kg) 30 minutes prior to the spermine injection. Data shown are infarct volume (mm$^3$) assessed quantitatively 48 hr after the intracortical spermine injection (mean±s.e., n=6–8/group). *P<0.05 vs spermine/vehicle.

There was brain tissue damage in animals given intracortical spermine or spermidine, but cell death was not observed after intracortically administered putrescine, a polyamine which cannot be degraded by polyamine oxidase to generate 3-aminopropanal (see FIG. 3). The quantities of 3-aminopropanal administered (25 $\mu$g per injection) were similar to the amounts produced endogenously during ischemia (approximately 350 $\mu$M assuming a volume of distribution of a typical middle cerebral artery infarction). Intracortical administration of these amounts of 3-aminopropanal caused significant cytotoxicity in the cerebral cortex. Systemic administration of the polyamine oxidase inhibitors chloroquine and aminoguanidine conferred significant protection against the development of spermine-mediated intracortical damage (see FIG. 4), suggesting that polyamine oxidase activity is necessary to mediate the cytotoxicity of extracellular spermine. Intracortical administration of aminoguanidine also conferred significant protection against intracortical spermine-mediated cell death (see FIG. 4), indicating that the cerebroprotective effects of the enzyme inhibitor occur locally in the brain cortex, and not via some unanticipated peripheral drug action. Of note, aminoguanidine failed to significantly attenuate the direct cytotoxicity of intracortical 3-aminopropanal (see FIG. 4), suggesting that the protective mechanism of aminoguanidine against spermine cytotoxicity is through inhibition of polyamine oxidase, and not by directly inhibiting the cytotoxicity of 3-aminopropanal.

Thus, increased extracellular levels of spermine, spermidine, or 3-aminopropanal (but not putrescine) are cytotoxic in vivo, in this case to cerebral cortical cells. Furthermore, this model provides a convenient assay for the activity of test compounds and compositions to inhibit 3-aminopropanal-mediated tissue damage. Test compounds or compositions may be administered in any of a variety of dosage formats (e.g., intravenous, intraperitoneal, oral, intramuscular, intracranial), either before or at various time periods after experimental introduction of 3-aminopropanal into tissue, such as brain. The activity of test compounds and compositions to antagonize the in vivo cytotoxic effects of the administered 3-aminopropanal may then be conveniently evaluated, for instance by vital staining to estimate the extent of induced cell death or tissue infarction.

3-Aminonpropanal Mediates Both Cellular Necrosis and Apoptosis in vivo

A series of experiments were undertaken to elucidate the endogenous mechanisms underlying tissue damage during ischemia Specifically, the fate of brain cells in animals subject to intracortical administration of polyamines or 3-aminopropanal was studied. Histopathologic examinations performed on brain tissue harvested 24 hr after intracortical 3-aminopropanal microinjection localized degenerative changes to the tissue surrounding the injection zone. Stereotactically guided microinjections of 3-AP or various polyamines were made into the cerebral cortex. Tissues were prepared for histology by anesthetizing the animals and then perfusing transcardially in sequence with saline (30 ml, pH=7.4), formaldehyde (100 ml, 4% in PBS, pH=6.5), then formaldehyde (100 ml, 4%, pH=8.5). Tissues were allowed to postfix for 30 minutes, then perfused with sucrose (50 ml, 20% in 0.1M PBS, pH=7.4). Brains were then removed, stored in sucrose overnight at 4° C., and sectioned into 10 mm thick sections. Deoxynucleotidyltransferase (TdT)-mediated dUTP-biotin nick end-labeling (TUNEL) staining was performed using a kit according to the manufacturers instructions (ApopTag, Oncor). Cells near the 3-aminopropanal injection site were necrotic, as evidenced by eosin-positive staining. Moreover, in the same region, cells were undergoing programmed cell death, as evidenced by TUNEL positive staining. These changes were not observed in the injection zone when either vehicle or putrescine was administered. Direct intracortical administration of spermine also caused cell necrosis and apoptosis, and this degeneration was significantly inhibited by administration of aminoguanidine. Thus, the accumulation of brain cell damage in vivo, in response to intracortical extracellular 3-aminopropanal administration, occurs through both cellular necrosis and programmed cell death.

EXAMPLE 3

In vitro Screening Assays for Agents to Prevent or Minimize Tissue Damage and Cell Death Following Ischemia 3-aminopropanal Induces Apoptosis in Glial Cells, but Cellular Necrosis in Neuronal Cells To directly investigate the cytotoxic mechanisms and corresponding signaling cascades induced by 3-aminopropanal, cultured human glial (HTB14) and neuronal (HTB11) cell lines were exposed to 3-aminopropanal. The glial cell line (HTB14) (Ponten and Macintyre, *Acta Pathol. Microbiol. Scand.* 74:465486, 1968) and neuronal cell line (HTB11) (Bluestein, *Proc. Natl. Acad. Sci. USA*

75:3965–3969, 1978) were obtained from the American Type Culture Collection (ATCC) and cultured in minimal Eagle's medium (MEM; Gibco), supplemented to 10% fetal bovine serum (FBS; Hyclone), 1 mM Na pyruvate (Sigma), 0.5% penicillin/streptomycin (Sigma), in a humidified atmosphere of 5% $CO_2$ in air at 37° C. For all experiments involving exposure to 3-aminopropanal, cells were grown in 96-well microtiter plates to 90–95% confluence. Prior to all experiments the medium was replaced with fresh serum-free medium (Opti-MEM I), in order to minimize interaction of 3-aminopropanal with serum proteins. For all experiments utilizing a short duration of 3-aminopropanal exposure (5 minutes to 2 hours in 96-well plates), the cells were washed at the times indicated, and then incubated in Opti-MEM I for up to 20 hours before assessment of cell viability. Assessment of involvement of caspase-1 and caspase-3 in cell death following 3-AP exposure was by pretreating cells with the caspase-1 inhibitor, Ac-YVAD-CMK (BACHEM), or the caspase-3 inhibitor, Ac-DEVD-CHO (Peptides International), for 3 hours followed by addition of 3-aminopropanal for 5 additional hours. DMSO controls were performed to assess for effects of solvent. Cell viability was measured by the metabolically-dependent reduction of 3-(4,5-dimethylthiazol-2-yl)-2,5-diphenyltetrazolium bromide (MTT) (Sigma) (Sieuwerts et al., *Eur. J. Clin. Chem. Clin. Biochem.* 33:813–823, 1995). Data are expressed as mean±s.d.; n=3–6 wells per condition, and experiments performed in triplicate.

Following 20 hr of incubation, the cytotoxic $LD_{50}$ for 3-aminopropanal was estimated as 275±10 $\mu M$ for the glial cell line, HTB-14, and 90±20 $\mu M$ for the neuronal cell line, HTB11. 3-Aminopropanal was somewhat more cytotoxic in primary rat astroglial cell cultures ($LD_{50}$=80±9 $\mu M$). A time course study revealed that 3-aminopropanal exposure for as little as 5 minutes was significantly cytotoxic to neuronal cells, but a longer exposure was required to mediate significant cytotoxicity in glial cells (see Table I below).

Table I. Time course study of cell viability after exposure to 3-aminopropanal. Gial or neruonal cell line cultures were exposed to an $LD_{100}$ concentration of 3-aminopropanal (750 or 350 $\mu M$, respectively) for the indicated time, then medium was replaced with serum-free (no 3-AP) for a total incubation time of 20 hrs. Cell viability was then determined by MTT assay (data shown are mean±s.e.). Cell viability was 100±4% for all times in vehicle-treated controls.

|  | Cell Viability (% alive) | |
| --- | --- | --- |
| Time (min) | Glial Cells (HTB14) | Neuronal Cells (HTB11) |
| 5 | 96 ± 3 | 29 ± 6 |
| 60 | 92 ± 1 | 13 ± 4 |
| 120 | 78 ± 7 | 6 ± 2 |
| 1200 | 5 ± 5 | 3 ± 1 |

This latent onset suggested that glial cell death might be dependent upon apoptosis-mediated pathways. In agreement with this possibility, an apoptosis-specific DNA fragmentation pattern was observed following exposure of HTB-14 glial cells to 3-aminopropanal, but not after corresponding exposure of cultured neuronal cells, HTB-11.

Additional evidence of apoptosis by flow cytometric detection of DNA strand breaks was obtained using the terminal deoxynucleotidyl taansferase mediated dUTP nick end labeling TUNEL) method (Gavrieli et al., *J. Cell. Biol* 119:493–501, 1992). Terminal deoxynucleotidyl transferase mediated dUTP nick end labeling (TUNEL) staining was performed on cell cultures treated with 3-aminopropanal, as indicated. Cells were harvested and collected by centrifugation at 1,500 rpm for 5 min. The pellets were fixed with 1×ORTHO Permeafix (Orthodiagnostics) at room temperature for 40 min. After washing with Dulbecco's phosphate-buffered saline containing 1% bovine serum albumin (PBS-BSA), cells were stained by the TUNEL method using the Oncor Apop Tag Direct Fluorescein kit (Oncor), in accordance with the manufacturer's instructions. A negative control was performed by preparing a reaction solution that was devoid of TdT. A Becton Dickinson flow cytometer was used for all analyses; five to ten thousand events (ungated) were collected according to a single color procedure.

In these experiments, 76% of the glial cells stained TUNEL-positive following 13 hours of exposure to 275 $\mu M$ 3-aminopropanal, whereas vehicle-treated control cells were uniformly TUNEL-negative. Multi-parameter flow cytometry revealed that glial cell populations exposed to 3-aminopropanal exhibited a decrease in cellular forward light scatter and an increase in side scatter, consistent with the typical cell shrinkage, chromatin condensation, and nuclear fragmentation of apoptosis. Apoptosis of glial cells was also confirmed by subdiploid staining with propidium iodide and with Annexing V/PI.

In contrast to the results in the glial cell line (HTB-14), 3-aminopropanal did not induce apoptosis in neuronal cell cultures (HTB11) using similar experimental methods. DNA samples from HTB11 or HTB14 cells (20–30×$10^6$ cells) were assayed for strand breakage by resuspending harvested cells (treated with 3-AP or control) in a reaction buffer containing proteinase K, and incubating overnight at 55° C. RNase was added to a final concentration of 50 mg/ml and the samples were incubated at 37° C. for one hour. DNA was extracted three times with phenol/chloroform and twice with chloroform and precipitated in two volumes of chilled 100% ethanol and 0.3M sodium acetate (pH 5.2). The DNA was resuspended in 50 $\mu l$ of $dH_2O$, fractionated by 1.5% agarose gel electrophoresis, and stained with SYBR Green I nucleic acid stain (Molecular Probes).

Electrophoresis of DNA prepared from 3-aminopropanal-treated neurons revealed no evidence of chromosomal DNA degradation. In addition, no increase in TUNEL-positivity under these conditions was observed, although a forward scatter/side scatter analysis revealed significant cell death after 3-aminopropanal treatment (55.7%), but not in vehicle-treated controls (9.1%).

There was also no evidence of apoptosis as measured with Annexin V, a method used to detect loss of cell membrane phospholipid asymmetry that has be associated with apoptosis. Annexin V/propidium iodide (PI) staining was performed using a kit in accordance to the manufacturer's instructions (Me Apoptosis Detection Kit, R&D Systems, Minneapolis). Cells were analyzed by flow cytometry within one hour of completion of staining. The AnnexinV-FITC and PI signals were quantitated independently according to a two-color flow cytometric procedure.

Apoptosis was induced in neuronal cells by exposure to camptothecin (Furuya et al., *Anticancer Res* 17:2089–2093, 1997) (15 $\mu g/ml$ for 20 hr) as assessed by TUNEL and Annexin V methods, indicating that the absence of apoptosis after 3-aminopropanal exposure was not due to some unanticipated generalized cellular defect in these neuron-like cells. Thus, in contrast to glial cells, exposure of neuronal cells to 3-aminopropanal causes primarily necrotic cell death.

The in vitro cell culture experiments described in this example provide convenient assays is for the activity of test compounds and compositions to inhibit 3-aminopropanal-mediated cytotoxicity, predictive of like benefits in mitigating tissue damage in vivo. Test compounds or compositions may be introduced simultaneously with, before or at various time periods after experimental introduction of 3-aminopropanal into the cell cultures, which may be glia-like (e.g., HTB-14), neuron-like (e.g., HTB-11) or typical of other cells or tissues subject to ischemic damage in vivo. The activity of test compounds and compositions to antagonize the in vitro a cytotoxic effects of the administered 3-aminopropanal may then be conveniently evaluated, for instance by staining to estimate the extent of induced cell death and further to characterize said cytotoxicity as cellular necrosis vs. apoptosis.

Figure 5:
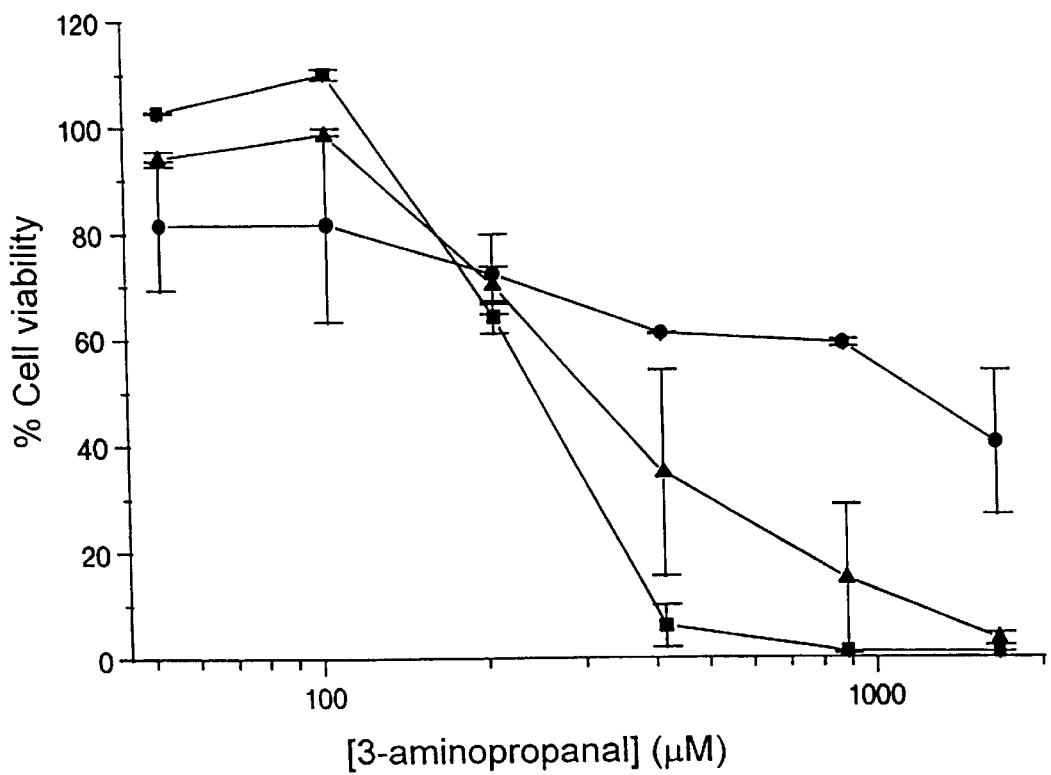
FIG. 5 shows that inhibition of ICE (caspase-1), but not of CPP-32 (caspase-3) blocked 3-aminopropanal-induced glial apoptosis in vitro. Cells were pretreated with the ICE (IL-1β converting enzyme) inhibitor (Ac-YVAD-CMK) at concentrations of 0.4 µM (triangles) or 40 µM (circles) for 3 hours, followed by treatment with 3-aminopropanal for an additional 5 hours, and analyzed for cell viability by the MTT assay. Controls consisted of DMSO-treated cells (squares) to assess for non-specific solvent effects. Data are mean±s.d., n=3 wells/experiment

Caspase-1 Plays a Role in the 3-aminopropanal-induced Apoptosis of Glial Cell Cultures The cysteine proteases ICE (Interleukin-1 beta Converting Enzyme; caspase-1) and cysteine protease P-32 (CPP-32; caspase-3) have been implicated in the cellular signaling pathways mediating apoptosis during cerebral ischemia (Bhat et al., *J. Neurosci.* 16:41464154, 1996; Loddick et al., *Neuroreport.* 7:1465–1468, 1996; Hara et al., *Proc. Natl. Acad. Sci. USA* 94:2007–2012, 1997; and Friedlander et al., *J. Exp. Med* 185:933–940, 1997). To investigate whether these proteases were required for the induction of apoptosis by 3-aminopropanal in glial cells, HTB14 cells were treated for three hours with a tetrapeptide ICE inhibitor (Ac-YVAD-CMK), or with a CPP-32 inhibitor (Ac-DEVD-CHO), followed by a five hour treatment with 3-aminopropanal. Treatment with the ICE inhibitor, but not the CPP-32 inhibitor, conferred dose-dependent inhibition of 3-aminopropanal-induced cell death (see FIG. 5), indicating that ICE proteases are required for 3-aminopropanal-induced apoptosis. These data give evidence for a specific role of ICE in the 3-aminopropanal-induced signaling that mediates apoptosis in glial cells, and further exemplify the utility of these in vitro screening assays for identifying compounds and compositions with activity in mitigating 3-aminopropanal-induced tissue damage.

EXAMPLE 4
In vivo Screening Assay for Compounds and Compositions with Activity in Mitigating Tissue Damage Following Ischemia
Administration of Polyamine Oxidase Inhibitors in vivo Attenuates 3-aminopronanal Production and Protects Against Ischemia-induced Tissue Damage The mechanism of ischemia-induced cell death and tissue damage introduced herein predicts that administration of polyamine oxidase inhibitors during cerebral ischemia in vivo will reduce both the accumulation of 3-aminopropanal and the volume of cerebral infarction. Accordingly, these end points were measured after administering two structurally distinct polyamine oxidase inhibitors to rats in the standardized model of permanent middle cerebral artery occlusion described above. Aminoguanidine, administered after the onset of cerebral ischemia (320 mg/kg i.p. 15 minutes post-ischemia, then 110 mg/kg i.p. every 8 hrs), significantly reduced the volume of cerebral damage (Cockroft et al., *Stroke* 27:1393–1398, 1996). Aminoguanidine administered by this established treatment protocol efficaciously prevented the increase of brain 3-aminopropanal levels (see Table II). Rats were subjected to permanent middle cerebral artery occlusion (n=4/group), and infarct volume measured 25 hours after the onset of ischemia as described above. Treated animals received either aminoguanidine (AG; 320 mg/kg i.p. 15 minutes post-ischemia, followed by 100 mg/kg i.p. every 8 hr), chloroquine (CQ; 25 mg/kg i.p. 15 minutes post-ischemia), or vehicle (saline, i.p.) given 15 minutes post-ischemia. Table II shows that two structurally distinct inhibitors of polyamine oxidase (AG and CQ) attenuate cerebral infarction and that AG can prevent the ischemia-associated local increase in 3-aminopropanal.

TABLE II

|  | Infarct Volume (mm$^3$) | Brain 3-aminopropanal level ($\mu$mol/g protein) |
| --- | --- | --- |
| Vehicle | 71 ± 24 | 13 ± 8 |
| Aminoguanidine | 12 ± 2*# | not detectable |
| Chloroquine | 27 ± 8* | not tested |

*$P < 0.05$ vs vehicle.
from (Cockroft et al., Stroke 27: 1393–1398, 1996)

In agreement with the above asserted mechanisms of tissue damage in ischemia, administration of chloroquine (a known inhibitor of polyamine oxidase) also protected against ischemia-induced tissue damage, even when such administration was delayed 15 minutes after occlusion of the middle cerebral artery (Table II). It was previously reported that the protective effects of aminoguanidine were not attributable to altering peripheral cardiovascular parameters that influence the volume of brain damage (Cockroft et al., *Stroke* 27:1393–1398, 1996). Similarly, chloroquine did not significantly alter systemic homeostatic responses to cerebral ischemia; physiological parameters measured before and during ischemia (blood pressure, heart rate, body temperature, arterial blood gases) did not differ between groups of subjects treated with vehicle or chloroquine. Thus, the cerebroprotective effects of chloroquine cannot be attributed to alterations in the peripheral cardiovascular response to cerebral ischemia, and seem instead to relate to the activity of chloroquine to inhibit PAO activity.

Previously, Iadecola and colleagues reported that iNOS is upregulated 24–48 hr after cerebral ischemia, and that delayed administration of aminoguanidine can prevent secondary NO-mediated brain damage in a delayed therapeutic window (Zhang et al., *Stroke* 27:317–323, 1996). The evidence of the present Examples, on the other hand, indicates that polyamine oxidase activity is upregulated much earlier after cerebral ischemia (within 2 hours), and that early administration of aminoguanidine inhibits the generation of 3-aminopropanal. Although the most direct interpretation of these data is that two structurally distinct inhibitors of polyamine oxidase prevented ischemic damage by preventing the formation of 3-aminopropanal, a series of additional experiments was performed to exclude other possibilities.

Addition of even suprapharmacological amounts of chloroquine (1 mM) failed to inhibit iNOS activity measured in RAW 264.7 cell lysates (iNOS activity in control cultures= 13300±250 DPM/$\mu$g protein vs. iNOS activity in chloroquine-treated cultures=11800±900 DPM/mg protein; $P>0.05$). Thus, these data exclude the unlikely possibility that chloroquine protection occurred through an unanticipated inhibition of iNOS.

When cell viability was measured in the presence of PAO inhibitors, it was observed that the LD$_{50}$ for 3-aminopropanal after overnight incubation in HTB11 cells was similar whether or not aminoguanidine or chloroquine were added. Thus, these data exclude the unlikely possibility that aminoguanidine or chloroquine might protect cells by directly interfering with the cytotoxic activity of 3-Aminopropanal.

When aminoguanidine was added to primary neuronal cultures treated with N-methy-D-aspartic acid (NMDA), no attenuation of cytotoxicity was observed (Table III). Thus, these data exclude the unlikely possibility that the mechanism of aminoguanidine protection is mediated via altering the sensitivity of cells to the cytotoxicity of glutamate. Cultured hippocampal neurons (12–15 days in vitro) were exposed to NMDA (500 $\mu$M) for 5 min in MEM (without serum) supplemented with glutamine (100 $\mu$M) and glycine (10 $\mu$M), rinsed in Earle's Basic Salt Solution, and incubated under standard conditions for 24 hr (37° C.). Neuronal survival was assessed microscopically, by counting a sample of cell somas for uptake vs. exclusion of trypan blue. Aminoguanidine or the non-competitive excitatory amino acid receptor antagonist, MK-801, was added just prior to NMDA and in the final rinse at the concentrations shown. Data are mean±s.e. of nine wells from three replicate experiments. Table III shows that aminoguanidine was not protective against NMDA neurotoxicity.

TABLE III

| | Cell viability (% dead) | | |
|---|---|---|---|
| [Aminoguanidine] ($\mu$M) | NMDA (500 $\mu$M) | MK-801 (20 $\mu$M) | Neurotoxicity (% dead) |
| 0 | − | − | 3 ± 1 |
| 0 | + | − | 88 ± 4 |
| 0 | + | + | 8 ± 3 |
| 1000 | + | − | 79 ± 4 |
| 1000 | − | − | 7 ± 2 |

A further experiment was conducted to determine whether 3-aminopropanal mediated cell death through induction of INOS activity. Addition of iNOS inhibitors (L-$N^G$-monomethylarginine (L-NMMA) or aminoguanidine) to 3-aminopropanal-treated glial cells failed to attenuate the development of TUNEL-positivity as measured by cytofluorography. Although these data have excluded a number of plausible alternative mechanisms through which aminoguanidine or chloroquine might protect against cerebral ischemia, it remains theoretically possible that other activities of chloroquine might additionally contribute to the observed protection against infarction (i.e., inhibition of free radical formation, phospholipase activity or protein synthesis). However, such alternative mechanisms do not account for the present chain of evidence showing that: 1) administration of inhibitors of polyamine oxidase activity limits the formation of 3-aminopropanal in the setting of ischemia; 2) 3-aminopropanal cytotoxicity cannot be blocked with chloroquine; and 3) either chloroquine or aminoguanidine prevented the brain damaging effects of either intracortical spermine or ischemia.

EXAMPLE 5

In vivo and in vitro Screening Assay Results: Active Compounds

Compounds Protective Against 3-aminopropanal-induced Cytotoxicity in vitro

Use of the in vitro screening assays described in Example 3 enables the identification of compounds with predicted clinical utility in ameliorating the extent of tissue damage following ischemia, particularly as therapeutic agents against the brain damage associated with stroke. Replicate glial cell cultures (HTB14) or neuronal cell cultures (HTB11) are cultured under conditions well-known in the art, and exposed to a concentration series of 3-aminopropanal (e.g., a 2×dilution series from 3200 $\mu$M to 25 $\mu$M). Test compounds are added simultaneously with, or at various times before or after addition of 3-aminopropanal, according to the detailed procedures of Example 3, allowing the test compounds to be evaluated for beneficial, protective effects (or for toxic effects to be noted) in an in vitro assay that is predictive of like ameliorative effects on the tissue damage attendant to focal ischemia in vivo. Use of glia-like and neuron-like cells in this in vitro assay is particularly adapted to modeling the cytotoxicity and tissue damage of cerebral ischemia or stroke. A variety of test compounds were evaluated by these methods at a concentration of 1.0 mM, with results summarized in Table IV below:

TABLE IV

| Effect of test compounds on 3-AP cytotoxicity | | |
|---|---|---|
| No effect or weakly protective | Toxic | Protective |
| Glial cell assay (HTB14) | | |
| putrescine | 3-(2-amino-2-oxoethyl)-4-methyl-5-(hydroxyethyl)-thiazolium bromide | p25 |
| aminoguanidine | | p27b |
| penicillamine | | 3-(2-methoxy-2-oxoethyl)-benzothiazolium bromide |
| 2,3-diamino-thiazolium O-mesitylenesulfonate | 2-mercaptoimidazole | 2-mercapto-1-methyl-imidazole |
| 3-(2-amino-2-oxoethyl)-4-methyl-thiazolium bromide | p117a | cysteine |
| thiamine HCl | p213a | N-acetylcysteine |
| 2-mercaptopyridine | | 2-mercaptoethylamine |
| 6-mercaptopurine riboside | | glutathione |
| p213b | | 1-(carboxymethyl)pyridinium chloride hydrazide |
| | | p27a |
| Neuronal cell assay (HTB11) | | |
| N-acetylcysteine | | p25 |
| glutathione | | p27a |
| | | p27b |
| | | cysteine | wherein:

p25 is 3-(2-phenyl-2-oxoethyl)-thiazolium bromide, and this compound also has been coded as PICVA-25;

p27b is 3-(2-phenyl-2-oxoethyl)-4-methyl-5-(hydroxyethyl)-thiazolium bromide p27a is N-(2-phenyl-2-oxoethyl)-pyridinium bromide, and this compound has also been coded as AP1 and as PICVA-27;

p213a is 2-(2-phenyl-2-oxoethyl)-2-mercaptoimidazole ether p213b is N,N'-bis-(2-phenyl-2-oxoethyl)-imidazolium bromide p117a is N-(2-phenyl-2-oxoethyl)-2-mercaptopyridinium bromide.

In an alternative embodiment of the screening assay of Example 3, various concentrations of the test compound (e.g. 10–1000 μM) are incubated with the indicator cells in presence of a fixed concentration fo 3-AP (e.g, 200 μM). The toxicity of the test compounds may be evaluated in parallel cultures incubated without 3-AP; generally, the desired test compound will show cellular toxicity at much higher doses than thos that confer protection against 3-AP (e.g., 10–10,000-fold). The results of such tests are summarized in Table V, below.

TABLE V

Effect of test compounds on 3-AP cytotoxicity

| No effect or weakly protective | Toxic or no effect | Protective (50% Effective dose; 50% Toxic dose) |
|---|---|---|
| Glial cell assay (HTB14) | | |
| AP6 | AP9 | p27a (425 μM; 5 mM) |
| AP2 | AP12 | AP21 (100 μM; not tested) |
| AP7 | AP19 | AP22 (199 μM; 1 mM) |
| YA1 | AP20 | |
| YA2 | AP23 | |
| AP18 | AP28 | |
| AP24 | 3,5-di-tert.-butyl-4-hydroxytoluene | |
| ascorbic acid | | |
| 32P | | | wherein:

AP6 is N-(2-phenyl-2-oxoethyl)-2-(2'-pyridine)-pyridinium bromide.

AP2 is N-(2-phenyl-2-oxoethyl)-quinolinium bromide.

AP7 is N-(2-phenyl-2-oxoethyl)-pyrazinium bromide.

YA1 is 2-phenyl-2-oxoethyl-dimethylphosphonate.

YA2 is N-(2-phenyl-2-oxoethyl)-triethylammonium bromide.

AP18 is N-(2-phenyl-2-oxoethyl)-4-tert.-butylpyridinium bromide.

AP24 is N-(2-phenyl-2-oxoethyl)-3-n-butylpyridinium bromide.

34P is pyridine-3,5-dicarboxylic acid.

AP9 is N-(2-phenyl-2-oxoethyl)-4-N,N-dimethylamino-pyridinium bromide.

AP12 is N-(2-phenyl-2-oxoethyl)-pyrazinium bromide.

AP19 is N-(2-phenyl-2-oxoethyl)-3-fluoropyridinium bromide.

AP20 is N-(2-phenyl-2-oxoethyl)-4-ethylpyridinium bromide.

AP23 is N-(2-phenyl-2-oxoethyl)-2,6-dihydroxymethylpyridinium bromide.

AP28 is N-(2-phenyl-2-oxoethyl)-3,5-diiodo-4-pyridinone.

AP21 is N-(2-phenyl-2-oxoethyl)-3,4-dicarboxyamide-pyridinium bromide.

AP22 is N-(2-phenyl-2-oxoethyl)-3-bromo-5-carboxypyridinium bromide.

Compounds Protective Against 3-aminopronanal-induced Cytotoxicity in vivo

Figure 6:
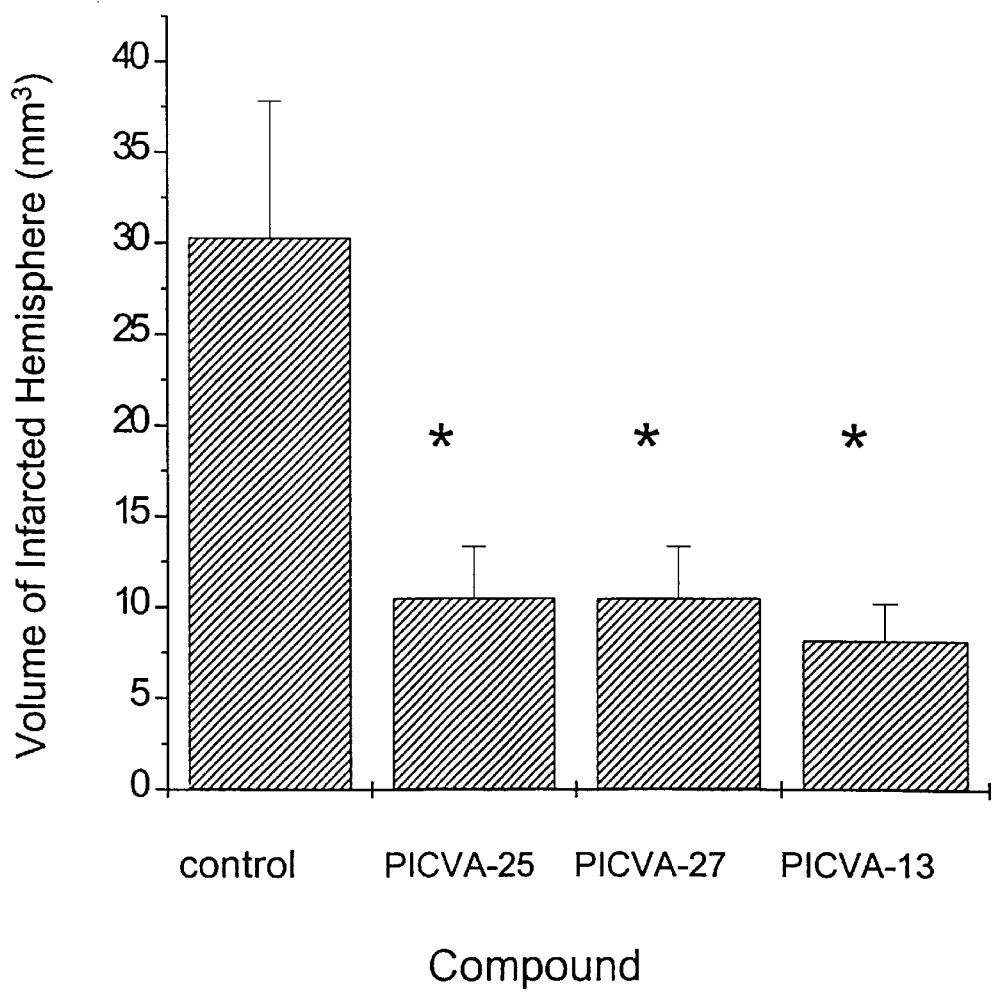
FIG. 6 shows cerebroprotection by three different phenylacyl pyridinium derivatives (PAPDs). Animals received either PBS vehicle (n=13) or PAPD treatment by i.p. injection beginning 15 minutes after the onset of ischemia PICVA-25 (n=9; total dose 200 mg/kg), PICVA-27 (n=12; total dose 200 mg/kg), PICVA-13 (n=8; total dose 400 mg/kg). Data shown are mean stroke (infarct) volumes expressed as mm$^3$±s.e.m. *P<0.05 by one way ANOVA.
Figure 7:
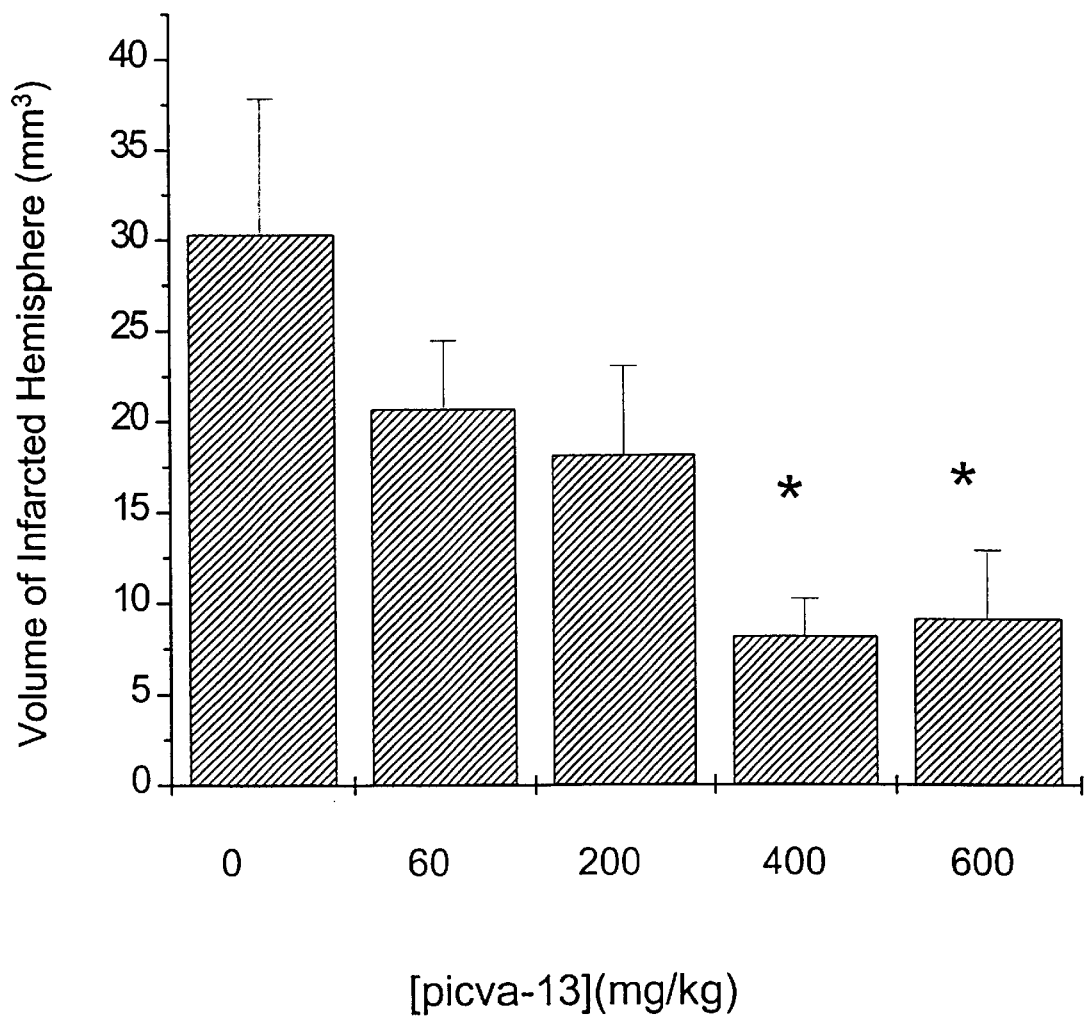
FIG. 7 shows a dose:response relationship for compound PICVA-13 in an in vivo screening assay for cerebroprotection following experimentally induced focal brain ischemia. Animals received either PBS vehicle (n=13) or PICVA-13 i.p. beginning at 15 minutes after the onset of ischemia PICVA-13 was administered at 60 mg/kg (n=6), 200 mg/kg (n=6), 400 mg/kg (n=11) or 600 mg/kg (n=13). Data shown are infarct volumes expressed as mm$^3$±s.e.m. *P<0.05 by one way ANOVA.
Figure 8:
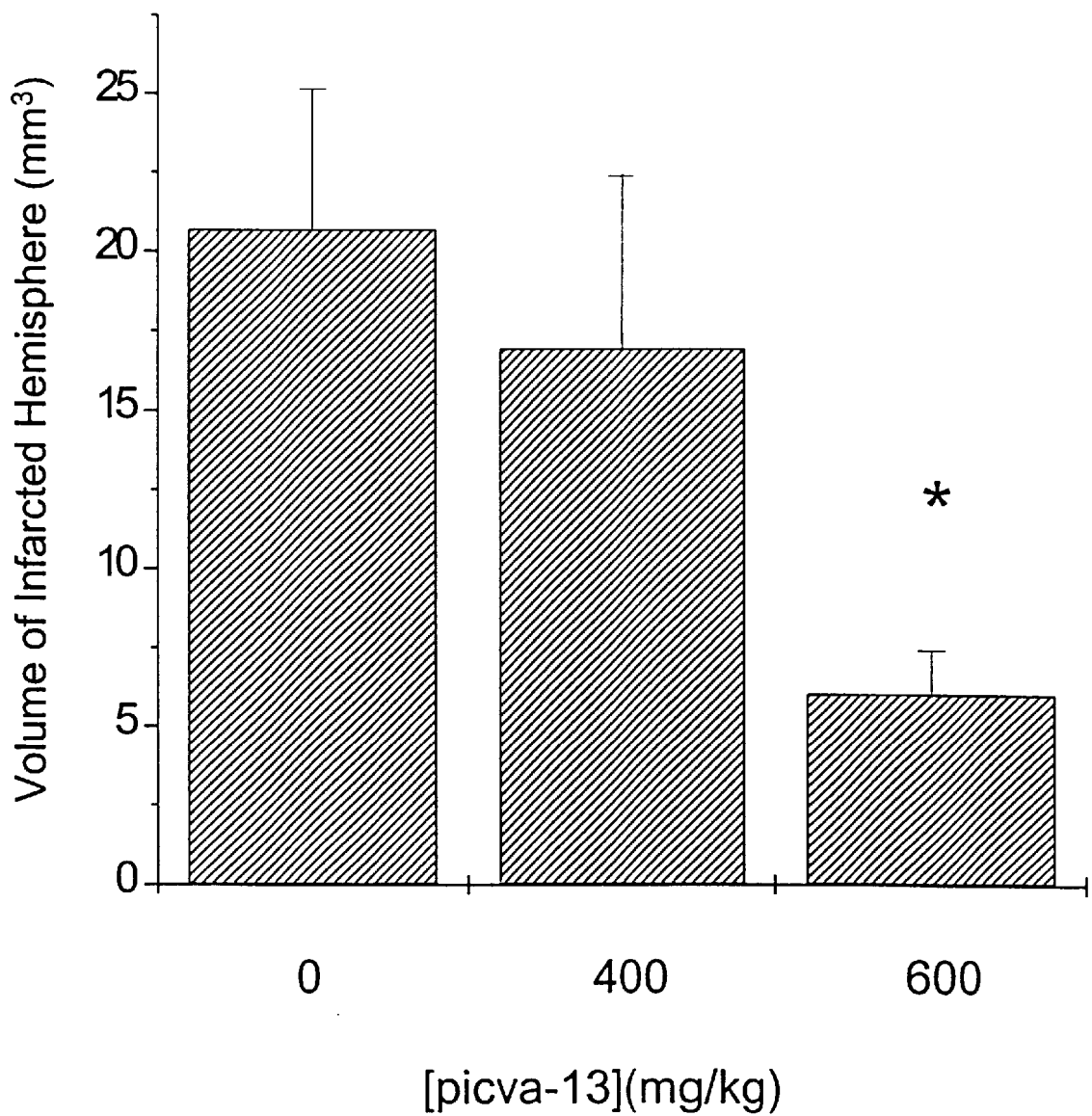
FIG. 8 shows that the beneficial, cerebroprotective effects of PICVA-13 treatment are available for at least two hours after ischemia begins. Animals received either PBS vehicle (n=10) or PICVA-13 beginning two hours after the onset of ischemia, at dose of 400 mg/kg (n=8) or 600 mg/kg (n=9). Data shown are infarct volumes expressed as mm$^3$±s.e.m. *P<0.05 by one way ANOVA.

Use of the in vivo screening assays described in Examples 2 and 4 enables the identification of compounds with predicted clinical utility in ameliorating the extent of tissue damage following ischemia, particularly as therapeutic agents against the brain damage associated with stroke. Use of these in vivo screening assays is particularly valuable to further validate the potential beneficial effects of compounds and compositions identified as pharmacologic inhibitors of 3-AP toxicity in the companion in vitro assays of Example 3. Three phenylacyl pyridinium derivatives identified in in vitro as inhibitors of 3-AP cytotoxicity were evaluated by the in vivo assay methods described above. As shown in FIG. 6, when either of three different phenylacyl pyridinium derivatives (designated PICVA-13, PICVA-25 and PICVA-27) were administered i.p. beginning 15 minutes after the onset of ischemia (operationally defined as the time of division of the MCA), the volume of brain tissue eventually infarcted was significantly reduced as compared to vehicle-treated controls. With compound PICVA-13, this protective effect was dose-dependent (see FIG. 7). The protective effect of compound PICVA-13 also was obtained at a dose of 600 mg/kg when PICVA-13 was administered as late as two hours after the onset of ischemia (see FIG. 8; 70% reduction in infarct size; $P<0.05$). This dose-dependent protection by PICVA-13 treatment was independent of systemic parameters known to influence the extent of brain damage in stroke (e.g., blood pressure, heart rate, temperature, serum glucose, and arterial pH, $Po_2$ and $Pco_2$.; which parameters sampled at 60 and 120 minutes after onset of ischemia did not differ significantly from baseline). Also, an index of brain edema did not differ between PICVA-13-treated and control treated subjects. This example provides evidence that pharmacologic inhibitors of 3-aminopropanal cytotoxicity can significantly limit the volume of brain damaged in experimental stroke, predictive of the utility of such agents as therapeutic agents for human clinical use.

Whole Animal Toxicity of Phenylacyl Pyridinium Compounds

In the in vivo screening tests reported above, appreciable mortality (25% and 38%, respectively) was associated with treatment with compounds PICVA-27 and PICVA-25; no deaths occurred in association with PICVA-13 treatment Further testing showed that no otherwise untreated mice died at the seven-day timepoint after administration of doses of PICVA-13 ranging from 1.0 mg/kg to 1000 mg/kg (two mice treated per dosage condition; 1.0, 10, 100, 500 and 1000 mg/kg). Male Balb/c mice weighing between 20 and 25 grams were treated with PICVA-13 by intraperitoneal injection, and the mice were observed for survival over the ensuing seven days. All mice survived and no mice exhibited overt signs of toxicity, demonstrating normal grooming and feeding over the observation period. This lack of toxicity established compound PICVA-13 as the preferred compound.

We claim:

1. An ischemia-damage mitigating salt of a compound, said compound having a formula 1:

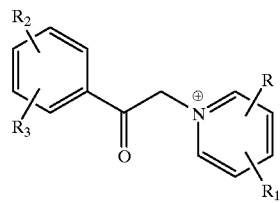

wherein R and $R_1$ are independently hydrogen, sulfamide, carboxyamide, cyano, straight or branched $C_{1-6}$ alkyl, straight or branched $C_{2-6}$ alkynyl, straight or branched $C_{1-6}$ alkoxy, a straight chain $C_{1-6}$ alkyl or a straight chain $C_{2-6}$ alkenyl having an ether link or an ester link, toluenyl, COOH, nitrate, or halide (Br, Cl, I, F), wherein at least one of R and $R_1$ is COOH, wherein $R_2$ and $R_3$ are independently hydrogen, sulfamide, carboxyamide, cyano, straight or branched $C_{1-6}$ alkyl, straight or branched $C_{2-6}$ alkynyl, straight or branched $C_{1-6}$ alkoxy, a straight chain $C_{1-6}$ alkyl or a straight chain $C_{2-6}$ alkenyl having an ether link or an ester link, toluenyl, COOH, nitrate, or halide (Br, Cl, I, F).

2. The ischemia-damage mitigating salt of claim 1 wherein $R_2$ and $R_3$ are both hydrogen.

3. The ischemia-damage mitigating salt of claim 1 wherein R and $R_1$ are each COOH, and $R_2$ and $R_3$ are both hydrogen.

4. The ischemia-damage mitigating salt of claim 1 wherein the compound is selected from the group consisting of 1-phenacyl-2,3-dicarboxypyridinium bromide; 1-phenacyl-2,4-dicarboxypyridinium bromide; 1-phenacyl-2,5-dicarboxypyridinium bromide; 1-phenacyl-2,6-dicarboxypyridinium bromide; 1-phenacyl-2,3-dicarboxyimidepyridinium bromide; 1-phenacyl-2,4-dicarboxyimidepyridinium bromide; 1-phenacyl-2,5-dicarboxyimidepyridinium bromide; and 1-phenacyl-2,6-dicarboxyimidepyridinium bromide.

5. A pharmaceutical composition comprising a salt of a compound from formula I in a pharmaceutically acceptable carrier, wherein formula I comprises:

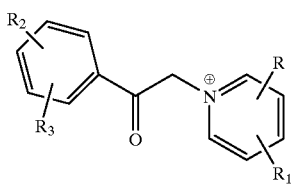

I wherein R and $R_1$ are independently hydrogen, sulfamide, carboxyamide, cyano, straight or branched $C_{1-6}$ alkyl, straight or branched $C_{2-6}$ alkenyl, straight or branched $C_{1-6}$ alkoxy, a straight chain $C_{1-6}$ alkyl or a straight chain $C_{2-6}$ alkenyl having an ether link or an ester link, toluenyl, COOH, nitrate, or halide (Br, Cl, I, F), wherein at least one of R and $R_1$ is COOH, wherein $R_2$ and $R_3$ are independently hydrogen, sulfamide, carboxyamide, cyano, straight or branched $C_{1-6}$ alkyl, straight or branched $C_{2-6}$ alkenyl, straight or branched $C_{1-6}$ alkoxy, a straight chain $C_{1-6}$ alkyl or a straight chain $C_{2-6}$ alkenyl having an ether link or an ester link, toluenyl, COOH, nitrate, or halide (Br, Cl, I, F).

6. The pharmaceutical composition of claim 5 wherein R and $R_1$ are meta to each other and to the heteroatom.

7. The pharmaceutical composition of claim 5 wherein R is COOH.

8. The pharmaceutical composition of claim 5 wherein $R_1$ is COOH.

9. The pharmaceutical composition of claim 5 wherein $R_2$ and $R_3$ are both hydrogen.

10. The pharmaceutical composition of claim 5 wherein R and $R_1$ are each COOH, and $R_1$ and $R_3$ are both hydrogen.

11. The pharmaceutical composition of claim 5 wherein the compound is selected from the group consisting of 1-phenacyl-2,3-dicarboxypyridinium bromide; 1-phenacyl-2,4dicarboxypyridinium bromide; 1-phenacyl-2,5-dicarboxypyridinium bromide; 1-phenacyl-2,6-dicarboxypyridinium bromide; 1-phenacyl-2,3-dicarboxyimidepyridinium bromide; 1-phenacyl-2,4-dicarboxyimidepyridinium bromide; 1-phenacyl-2,5-dicarboxyimidepyridinium bromide; and 1-phenacyl-2,6-dicarboxyimidepyridinium bromide.

12. A method for inhibiting tissue damage caused by ischemia, comprising administering an effective amount of a salt of a compound of formula I, wherein formula I comprises:

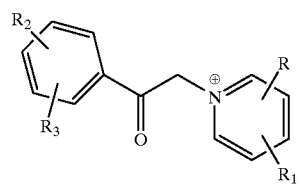

I wherein R and $R_1$ are independently hydrogen, sulfamide, carboxyamide, cyano, straight or branched $C_{1-6}$ alkyl, straight or branched $C_{2-6}$ alkenyl, straight, or branched $C_{1-6}$ alkoxy, a straight chain $C_{1-6}$ alkyl or a straight chain $C_{2-6}$ alkenyl having an ether link or an ester link, toluenyl, COOH, nitrate, or halide (Br, Cl, I, F), wherein at least one of R and $R_1$ is COOH, wherein $R_2$ and $R_3$ are independently hydrogen, sulfamide, carboxyamide, cyano, straight or branched $C_{1-6}$ alkyl, straight or branched $C_{2-6}$ alkenyl, straight or branched $C_{1-6}$ alkoxy, a straight chain $C_{1-6}$ alkyl or a straight chain $C_{2-6}$ alkenyl having an ether link or an ester link, toluenyl, COOH, nitrate, or halide (Br, Cl, I, F).

13. The method of claim 12 wherein R and $R_1$ are meta to each other and to the heteroatom.

14. The method of claim 12 wherein R is COOH.

15. The method of claim 12 wherein $R_1$ is COOH.

16. The method of claim 12 wherein $R_2$ and $R_3$ are both hydrogen.

17. The method of claim 12 wherein R and $R_1$ are each COOH, and $R_2$ and $R_3$ are both hydrogen.

18. The method of claim 12 wherein the compound is selected from the group consisting of 1-phenacyl-2,3-dicarboxypyridinium bromide; 1-phenacyl-2,4-dicarboxypyridinium bromide; 1-phenacyl-2,5-dicarboxypyridinium bromide; 1-phenacyl-3,5-dicarboxypyridinium bromide (AP5); 1-phenacyl-2,6-dicarboxypyridinium bromide; 1-phenacyl-2,3-dicarboxyimidepyridinium bromide; 1-phenacyl-2,4-dicarboxyimidepyridinium bromide; 1-phenacyl-2,5-dicarboxyimidepyridinium bromide; and 1-phenacyl-2,6-dicarboxyimidepyridinium bromide.

19. An ischemia-damage mitigating compound or salt thereof, said compound having a formula I:

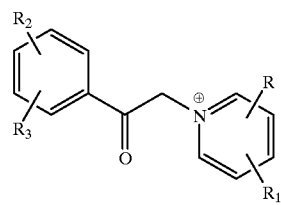

wherein R and $R_1$ are independently hydrogen, sulfamide, carboxyamide, cyano, straight or branched $C_{1-6}$ alkyl, straight or branched $C_{2-6}$ alkynyl, straight or branched $C_{1-6}$ alkoxy, a straight chain $C_{1-6}$ alkyl or a straight chain $C_{2-6}$ alkenyl having an ether link or an ester link, toluenyl, COOH, nitrate, or halide (Br, Cl, I, F), wherein at least one of R and $R_1$ is COOH, wherein $R_2$ and $R_3$ are independently hydrogen, sulfamide, carboxyamide, cyano, straight or branched $C_{1-6}$ alkyl, straight or branched $C_{2-6}$ alkynyl, straight or branched $C_{1-6}$ alkoxy, a straight chain $C_{1-6}$ alkyl or a straight chain $C_{2-6}$ alkenyl having an ether link or an ester link, toluenyl, COOH, nitrate, or halide (Br, Cl, I, F).

20. The ischemia-damage mitigating compound or salt thereof of claim 19 wherein R and $R_1$ are both not hydrogens and are meta to each other and to the heteroatom.

21. A pharmaceutical composition comprising a compound or salt thereof of claim 19 in a pharmaceutically acceptable carrier.

22. A method of inhibiting tissue damage caused by ischemia, comprising administering an effective amount of a compound or salt thereof of claim 19.

23. The ischemia-damage mitigating salt of claim 1, wherein R and $R_1$ are meta to each other and to the heteroatom.

24. The ischemia-damage mitigating salt of claim 23, wherein $R_2$ and $R_3$ are both hydrogen.

25. The ischemia-damage mitigating salt of claim 24, wherein R and $R_1$ are each COOH.

* * * * *